US 8,454,641 B2

(12) United States Patent
Fukuzawa

(10) Patent No.: US 8,454,641 B2
(45) Date of Patent: Jun. 4, 2013

(54) LANCET DEVICE

(75) Inventor: Masahiro Fukuzawa, Kyoto (JP)

(73) Assignee: Arkray, Inc. (JP)

( * ) Notice: Subject to any disclaimer, the term of this patent is extended or adjusted under 35 U.S.C. 154(b) by 962 days.

(21) Appl. No.: 11/995,448

(22) PCT Filed: Jul. 28, 2006

(86) PCT No.: PCT/JP2006/314994
§ 371 (c)(1),
(2), (4) Date: Jan. 11, 2008

(87) PCT Pub. No.: WO2007/013594
PCT Pub. Date: Feb. 1, 2007

(65) Prior Publication Data
US 2010/0298856 A1    Nov. 25, 2010

(30) Foreign Application Priority Data

Jul. 29, 2005  (JP) ................................. 2005-221924

(51) Int. Cl.
*A61B 17/32*   (2006.01)
*A61B 17/14*   (2006.01)

(52) U.S. Cl.
USPC ........................................................ 606/181

(58) Field of Classification Search
USPC ........... 606/181–183; 600/573–584; 660/181, 660/182, 183
See application file for complete search history.

(56) References Cited

U.S. PATENT DOCUMENTS

| 5,628,764 A | 5/1997 | Schraga |
| 5,916,230 A * | 6/1999 | Brenneman et al. .......... 606/172 |
| 6,090,124 A | 7/2000 | Weekes |
| 2003/0050608 A1 * | 3/2003 | Brown ........................... 604/198 |
| 2006/0178686 A1 * | 8/2006 | Schraga ....................... 606/181 |

FOREIGN PATENT DOCUMENTS

| EP | 1 815 792 A1 | 8/2007 |
| JP | 2000-245717 | 9/2000 |
| JP | 2000-516496 | 12/2000 |
| JP | 2004-057490 A | 2/2004 |
| JP | 2004-113580 A | 4/2004 |
| JP | 2004-329248 A | 11/2004 |
| JP | 2005-021291 A | 1/2005 |

(Continued)

OTHER PUBLICATIONS

"Summons to attend oral proceedings pursuant to Rule 115(1) EPC" of the corresponding EP patent application No. 06 781 904.5, dated Jan. 19, 2011.

*Primary Examiner* — S. Thomas Hughes
*Assistant Examiner* — Katherine M. Shi
(74) *Attorney, Agent, or Firm* — Studebaker & Brackett PC; Donald R. Studebaker

(57) ABSTRACT

A lancet device is configured for performing a puncture by mounting a lancet including a puncture needle to the tip of a puncture body holder. The lancet device has a simple configuration that makes it possible to strengthen the retaining force for retaining the lancet when the lancet is used. In the lancet device, an insertion portion of a puncture body that is inserted into a mounting portion of the puncture body holder is retained by means of the frictional force. A fastening member provided in a main body side makes contact with the outer peripheral portion of the mounting portion of the puncture body holder and inwardly fastens the mounting portion when the fastening member is moved in the puncture direction relative to the puncture body holder.

21 Claims, 14 Drawing Sheets

FOREIGN PATENT DOCUMENTS

| | | |
|---|---|---|
| JP | 3821490 | 6/2006 |
| WO | WO-98/06331 | 2/1998 |
| WO | WO-2004/043258 A1 | 5/2004 |
| WO | WO-2006/046570 | 5/2006 |

* cited by examiner

LANCET DEVICE

BACKGROUND OF THE INVENTION

1. Field of the Invention

The present invention relates to a lancet device used for producing a punctured wound on the skin when fluid or the like is obtained through the skin.

2. Background Information

With the growing number of diabetic patients, such cases are increasing that the diabetic patents measure the blood glucose level for themselves and perform self-monitoring its variation at their residences or the like. In view of the situation, a lancet device with a puncture needle has been produced, which is capable of obtaining blood necessary for measuring the blood glucose level by easily producing a punctured wound on the tip of a finger or the like when the blood is obtained for measuring the blood glucose level.

The lancet device includes a puncture needle on the tip thereof. The puncture needle is shot by means of the spring force while the tip of the lancet device is put on the tip of a finger or the like, and is protruded from the tip of the lancet device so that the protruded length corresponds to a few millimeters to 2.0 millimeters. With the above operation, the tip of a finger or the like is cut by the puncture needle and blood bleeding from the punctured wound is obtained. Then, the obtained blood is dropped on a sensor portion or the like of a glucose meter. Thus, it is possible to measure the glucose level.

As described above, this type of lancet device includes a puncture needle for producing a punctured wound on the tip of a finger or the like of a patient. Because of this, there has been a risk that especially the older people with poor eyesight or the like get hurt by mishandling the puncture needle.

In view of this, a so-called safety lancet device has been produced. The safety lancet device employs a configuration that a puncture needle is not exposed out of the main body if it is not needed (See Japanese Patent Application Publication No. 2000-245717 (disclosed on Sep. 12, 2000)).

For example, the Patent Document 1 discloses a lancet device including a puncture needle cartridge and a lancet device body that the puncture needle cartridge is detachably/reattachably mounted to the tip thereof. The lancet device body includes an elongated housing, a plunger, a regulator, a puncture controller, a set controller, a first coil spring for urging the plunger in a front end direction, and a second coil spring for urging the plunger in a base end direction. The housing is composed of a housing body and a cap-shaped member that is provided in the base end portion of the housing body.

According to the configuration, the puncture needle cartridge is detachably/reattachably mounted to the tip of the housing. Therefore, it is possible to replace the puncture needle safely, easily and promptly.

SUMMARY OF THE INVENTION

Problems the Invention is to Solve

However, the above conventional lancet device has a following problem. Specifically, in the lancet device disclosed on the above described publication, the base end portion of the lancet is inserted into a cylindrical mounting portion of the plunger that is included in the puncture needle body when the puncture needle cartridge is mounted to the lancet device body from the front end portion side of the lancet device body. Here, the outer diameter of the base end portion of the lancet and the inner diameter of the mounting portion of the plunger are formed in approximately the same dimension. Therefore, when the base end portion of the lancet is inserted into the mounting portion of the plunger, friction is generated between them. The lancet is thus retained in the lancet device body and is prevented from dropping out of the puncture by means of the frictional force. However, the retaining force for the lancet may not be able to be maintained only by depending on the frictional force generated when the base end portion of the lancet is inserted into the opening with approximately the same dimension as the base end portion.

An object of the present invention is to provide a lancet device with a simple configuration that makes it possible to further strengthen the retaining force for the lancet during use than ever before.

Means to Solve the Problems

The lancet device in accordance with a first aspect of the present invention is a lancet device that a lancet having a puncture needle is mounted to a tip thereof and that is configured to perform a puncture by moving the puncture needle forward in a puncture direction. The lancet device includes the lancet, a lancet holder, and a fastening member. The lancet holder includes a mounting portion into that a base end portion of the lancet is inserted thereinto, and the mounting portion retains the lancet. The fastening member is configured to make contact with an outer peripheral surface of the mounting portion of the lancet holder and fasten the lancet holder in a direction intersectional to the puncture direction when the fastening member is moved relative to the lancet holder in the puncture direction.

With this configuration, when the lancet holder retaining the lancet to be attached to the mounting portion of the lancet holder is moved forward or backward in the puncture direction, the fastening member makes contact with the outer peripheral surface of the lancet holder, and the lancet holder is elastically deformed inwardly. Thus generated pressure increases the frictional force between the lancet and the lancet holder, and accordingly the lancet is retained.

Here, when the outer diameter of the base end portion of the lancet and the inner diameter of the mounting portion of the lancet holder are formed in approximately the same dimension, for instance, the frictional force is generated between the mounting portion of the lancet holder and the base end portion of the lancet.

In the conventional lancet devices, the lancet is retained in the main body side including the lancet holder only by means of the frictional force generated by regulating the dimensions of the above both members. However, when the lancet and the lancet holder are made of a resin or the like, for instance, the sufficient retaining force may not be achieved only by means of the retaining force that depends only on the frictional force, because the dimensions may be varied by dilation and contraction, wearing, or the like with temperature change. In this case, there is a risk that the lancet is dropped out of the lancet holder when a puncture is performed.

In the lancet device of the present invention, when the lancet is retained in the lancet holder, the frictional force generated between the lancet and the lancet holder is increased by the fastening pressure generated when the lancet holder and the fastening member make contact with each other.

Because of this, it is possible to ensure the sufficient retaining force, for example, when a puncture is performed, compared to the conventional lancet devices that retains a lancet only by means of the frictional force. In addition, it is possible to achieve a safer lancet device with a simple configuration in which a fastening portion for making contact with the outer peripheral side of the lancet holder is provided.

A lancet device in accordance with a second aspect of the present invention is the lancet device according to the first aspect of the present invention, and the outer diameter of the base end portion of the lancet and inner diameter of the mounting portion of the lancet holder are formed in approximately the same dimension.

Here, the lancet and the lancet holder are formed such that the outer diameter of the base end portion of the lancet and the inner diameter of the mounting portion of the lancet holder have approximately the same dimension.

With this configuration, the base end portion of the lancet that is inserted into the mounting portion of the lancet holder makes contact with the inner peripheral surface of the mounting portion of the lancet holder. Because of this, it is possible to generate the frictional force by the pressure generated between the lancet and the lancet holder. As a result, it is possible to ensure the first-phased retaining force with respect to the lancet in the lancet device of the present invention.

A lancet device in accordance with a third aspect of the present invention is the lancet device according to the first or second aspect of the present invention, and the outer peripheral surface of the mounting portion of the lancet holder and the fastening member are configured to make contact with each other by moving the lancet holder to the rear side in the puncture direction relative to the fastening member when the lancet holder is fastened.

Here, for example, the lancet is inserted into mounting portion of the lancet holder when the lancet is mounted, and the lancet holder is further moved to the rear side in the puncture direction after the lancet is mounted to the mounting portion. Accordingly, the fastening member is made contact with the outer peripheral surface of the mounting portion of the lancet holder.

With this configuration, it is possible to fasten the lancet holder as a following step of a series of operation performed when the lancet is mounted to the mounting portion. Therefore, it is possible to enhance operability when the lancet is mounted and it is also possible to ensure the sufficient retaining force for retaining the lancet when used. In addition, it is necessary to only move the lancet backward in the puncture direction in a process from a step of mounting the lancet to the lancet holder to a step of fastening the lancet to the lancet holder. Accordingly, it is possible to achieve a lancet device in which the sufficient retaining force is easily ensured.

A lancet device in accordance with a fourth aspect of the present invention is the lancet device according to the third aspect of the present invention, and the fastened state of the lancet holder is configured to be released by moving the lancet holder to the front side in the puncture direction with respect to the fastening member when the lancet is removed from the lancet holder.

Here, in a lancet device that a lancet is mounted to a lancet holder by moving the lancet to the rear side in the puncture direction and is then fastened, when the lancet is disposed after a puncture is performed, the fastened state is released by moving the lancet holder to the front side in the puncture direction with respect to the fastening member.

With this configuration, the fastened state in the lancet holder is easily released only by moving the lancet in an opposite direction from the direction in which the lancet is mounted (i.e., front side in the puncture direction), and accordingly it is possible to retain the lancet only by means of the frictional force. Here, it is possible to easily remove the lancet from the lancet holder by further moving the lancet to the front side in the puncture direction. As a result, while the large retaining force is ensured only when the lancet is used, it is possible to pull the lancet out of the lancet holder after the retaining force is weakened when the lancet is disposed. Accordingly, it is also possible to enhance operability when the lancet is disposed.

A lancet device in accordance with a fifth aspect of the present invention is the lancet device according to the third or fourth aspect of the present invention, and a taper portion is formed in a tip of the mounting portion of the lancet holder on the front side in the puncture direction so that the outer diameter of the mounting portion becomes larger toward the front side in the puncture direction.

Here, the taper portion that the outer diameter thereof is formed to be larger toward the front side in the puncture direction is formed in the end portion of the mounting portion of the lancet holder on the front side in the puncture direction.

With this configuration, when the lancet holder is moved to the rear side in the puncture direction relative to the fastening member, the taper portion formed in the mounting portion of the lancet holder is moved while it makes contact with the inner side of the fastening member. Thus, it is possible to inwardly fasten the mounting portion of the lancet holder. As a result, it is possible to achieve a fastening effect in the lancet holder with a simple configuration in which only the shape of the portion that the fastening member makes contact with the lancet holder is devised.

A lancet device in accordance with a sixth aspect of the present invention is the lancet device according to the first or second aspect of the present invention, and the outer peripheral surface of the mounting portion of the lancet holder and the fastening member are configured to make contact with each other by relatively moving the fastening member to the rear side in the puncture direction relative to the lancet holder when the lancet holder is fastened.

Here, for example, the lancet is inserted into the mounting portion of the lancet holder when the lancet is mounted, and the fastening member is then moved to the rear side of the lancet holder in the puncture direction after the lancet is mounted to the mounting portion. Accordingly, the fastening member is made contact with the outer peripheral surface of the mounting portion of the lancet holder.

With this configuration, it is possible to fasten the lancet holder by a simple operation that the fastening member is only moved after the lancet is mounted. Therefore, it is possible to enhance operability when the lancet is mounted, and it is also possible to ensure the sufficient retaining force for retaining the lancet.

A lancet device in accordance with a seventh aspect of the present invention is the lancet device according to the six aspect of the present invention, and the fastened state of the lancet holder is configured to be released by moving the fastening member to the front side in the puncture direction relative to the lancet holder when the lancet is removed from the lancet holder.

Here, in a lancet device that the lancet is mounted to the lancet holder by moving the lancet to the rear side in the puncture direction and the lancet holder is then fastened by moving the fastening member to the rear side in the puncture direction with respect to the lancet holder, when the lancet is disposed after a puncture is performed, the fastened state is released by moving the fastening member to the front side in the puncture direction with respect to the lancet holder.

With this configuration, it is possible to easily release the fastened state in the lancet holder and to produce the state that the lancet is retained only by means of the frictional force, only by moving the lancet to an opposite direction (i.e., front side in the puncture direction) from the direction when the fastened state is produced after the lancet is mounted. Here, it is possible to easily remove the lancet from the lancet holder by further moving the lancet to the front side in the puncture direction. As a result, while the large retaining force is ensured only when the lancet is used, it is possible to pull the lancet out of the lancet holder after the retaining force is weakened when the lancet is disposed. Accordingly, it is also possible to enhance operability when the lancet is disposed.

A lancet device in accordance with an eighth aspect of the present invention is the lancet device according to the sixth or seventh aspect of the present invention, and a taper portion is formed in a tip of the fastening member on the front side in the puncture direction so that the inner diameter of the fastening member becomes smaller toward the front side in the puncture direction.

Here, the taper portion whose inner diameter becomes smaller toward the front side in the puncture direction is formed in the end portion of the fastening member on the front side in the puncture direction.

With this configuration, when the lancet holder is moved to the front side in the puncture direction relative to the fastening member, the mounting portion of the lancet holder moves such that it mounts on the inner side of the above described taper portion. Accordingly, it is possible to inwardly fasten the mounting portion of the lancet holder. As a result, it is possible to achieve a fastening effect in the lancet holder with a simple configuration in which only the shape of the portion that the fastening member makes contact with the lancet holder is devised.

A lancet device in accordance with a ninth aspect of the present invention is the lancet device according to one of the first to eighth aspects of the present invention, and the fastening member is configured to elastically deform the mounting portion of the lancet holder making contact with the fastening member in a direction intersectional to the puncture direction when the lancet holder is fastened.

Here, the lancet holder is fastened by elastically deforming the mounting portion of the lancet holder that makes contact with the fastening member.

With this configuration, for example, when the fastened state of the lancet holder is released at the same time as the removal of the lancet after a puncture is performed, the shape of a elastically deformed portion of the mounting portion of the lancet holder is restored to the original shape. Accordingly, it is possible to easily restore to the state that the lancet is retained in the lancet holder only by means of the frictional force. As a result, it is possible to achieve a structure that the fastening force is generated in the lancet holder only when necessary.

A lancet device in accordance with a tenth aspect of the present invention is the lancet device according to one of the first to ninth aspects of the present invention, and a portion of the base end portion of the lancet to be inserted into the mounting portion of the lancet holder is formed to have the uniform outer diameter in the puncture direction.

Here, the diameter of the base end portion of the lancet is uniformly formed in the puncture direction. Therefore, for the purpose of retaining the base end portion of the lancet, which is inserted into the mounting portion of the lancet holder, it is necessary to retain the base end portion of the lancet in the lancet holder by means of the frictional resistance generated between the both by increasing the area of the mounting portion of the lancet holder that makes contact with the base end portion of the lancet.

In the lancet device of the present invention, the retained state is produced by the frictional force generated between the lancet and the lancet holder, and the pressure is further applied by the fastened state produced by the fastening member. Thus, the frictional force is increased.

With the configuration, even when the diameter of a portion of the base end portion of the lancet, which is retained in the lancet holder, is uniformly formed, it is possible to ensure the sufficient retaining force when the lancet device is used by increasing the frictional force with the fastening pressure applied by the fastening member.

A lancet device in accordance with an eleventh aspect of the present invention is the lancet device according to one of the first to tenth aspects of the present invention, and the lancet includes a puncture body, a casing portion and an engaging portion. The casing portion has a tubular portion and an opening, and the tubular portion is configured to accommodate the puncture body so that the puncture body is allowed to move back and forth in the puncture direction, and the opening is formed in an end portion of the casing portion on a protruding side of the puncture needle. The engagement portion is configured to retain the puncture body in the interior of the casing portion so that the puncture body is not allowed to move back and forth in the puncture direction when the puncture body is removed from the lancet holder. In addition, the retaining force for retaining the lancet in the lancet holder after the lancet holder is fastened by the fastening member is smaller than the retaining force by the engaging portion.

With this configuration, an engagement state is produced in the engagement portion when the lancet is removed from the lancet holder after a puncture is performed, and then the fastened state produced by the fastening member is released. Thus, it is possible to prevent the puncture needle from being exposed when the lancet is removed from the main body side after a puncture is performed. Accordingly, it is possible to provide a safer lancet.

A lancet device in accordance with a twelfth aspect of the present invention is the lancet device according to the eleventh aspect of the present invention, and the retaining force for retaining the lancet in the lancet holder after the lancet holder is fastened by the fastening member is larger than the force necessary for engaging the engaging portion.

With this configuration, in such a situation that the lancet is disposed, it is possible to prevent the fastened and retained state produced by the fastening member from being released until the engaged state is produced in the engaging portion. As a result, it is possible to release the fastened state while the puncture body is retained in the casing portion by completing the engaged state in the engaging portion by the time when the lancet is removed from the lancet holder.

A lancet device in accordance with a thirteenth aspect of the present invention is the lancet device according to one of the first to twelfth aspects of the present invention, and further includes an urging member that is provided between the fastening member and the lancet holder and is configured to apply the urging force toward the fastening side of the lancet holder in the puncture direction.

Here, the urging member that applies the urging force for keeping the fastening force is provided between the puncture body holder and the fastening member, both of which make contact with each other and produce the fastened state.

With this configuration, it is possible to prevent the urging member from releasing the fastened state even after the outer peripheral portion of the puncture body holder is inwardly fastened. Therefore, it is possible to stably keep the fastened state.

A lancet device in accordance with a fourteenth aspect of the present invention is the lancet device according to one of the first to thirteenth aspects of the present invention, and the lancet holder retains the base end portion of the lancet by means of the frictional force.

With this configuration, the lancet device functions as a mechanism for retaining lancet in the lancet holder, and combines the first-phased retaining force, which is defined as the frictional force generated when the lancet is inserted into the lancet holder, and the second-phased retaining force, which is defined as the strengthened frictional force that is generated by applying the fastening pressure by the fastening member to the first-phased retaining force. As a result, it is possible to further increase the retaining force in the lancet holder.

A lancet device in accordance with a fifteenth aspect of the present invention is the lancet device according to one of the first to fourteenth aspects of the present invention, and a groove portion is formed on the surface of the base end portion to be along the puncture direction.

With this configuration, when the cap formed on the opposite side from the base end portion in the lancet is torsionally-sheared, the groove portion formed in the base end portion functions as resistance to rotation of the lancet while the lancet is retained in the lancet holder. Thus, it is possible to prevent the retained state of the lancet in the lancet holder from being loosened. In addition, it is possible to further effectively prevent rotation of the lancet in the lancet holder by forming a convex portion and/or a slit on the mounting portion side of the lancet holder for retaining the base end portion of the lancet so that the convex portion and/or the slit corresponds to the above described groove portion.

A lancet device in accordance with a sixteenth aspect of the present invention is the lancet device according to one of the first to fifteenth aspects of the present invention, and a plurality of concave-convex portions are formed on the surface of the base end portion.

With this configuration, the frictional force to be generated between the mounting portion of the lancet holder and the lancet is increased by forming the concave-convex portions such as the satin finished surface on the surface of the base end portion of the lancet. Accordingly, it is possible to more tightly fasten the lancet in the lancet holder in the rotational direction and the puncture direction.

A lancet device in accordance with a seventeenth aspect of the present is the lancet device according to one of the first to sixteenth aspects of the present invention, and the base end portion includes a concave portion (or a convex portion) in a portion thereof fastened by the fastening member, and the fastening member includes a convex portion (or a concave portion) engaging with a concave portion (or a convex portion).

With this configuration, the lancet is retained in the lancet holder by means of engagement between the concave portion and the convex portion, and the engaging portion is further fastened by the fastening member. Thus, it is possible to further tightly retain the lancet in the lancet holder.

DETAILED DESCRIPTION OF THE PREFERRED EMBODIMENTS

A lancet device (puncture device) 10 in accordance with an embodiment of the present invention will be hereinafter explained with reference to FIGS. 1 to 9.

Entire Configuration of Lancet Device 10

The lancet device 10 in accordance with an embodiment of the present invention is a device used for taking fluid from a diabetic patient when measurement of the blood glucose level or the like is performed for the patient. When the lancet device 10 is used, a puncture wound is formed on the skin by protruding a puncture needle 21 (see FIG. 4) from an opening formed on a tip of the lancet device 10 while the tip is press-contacted with the skin.

Figure 1:
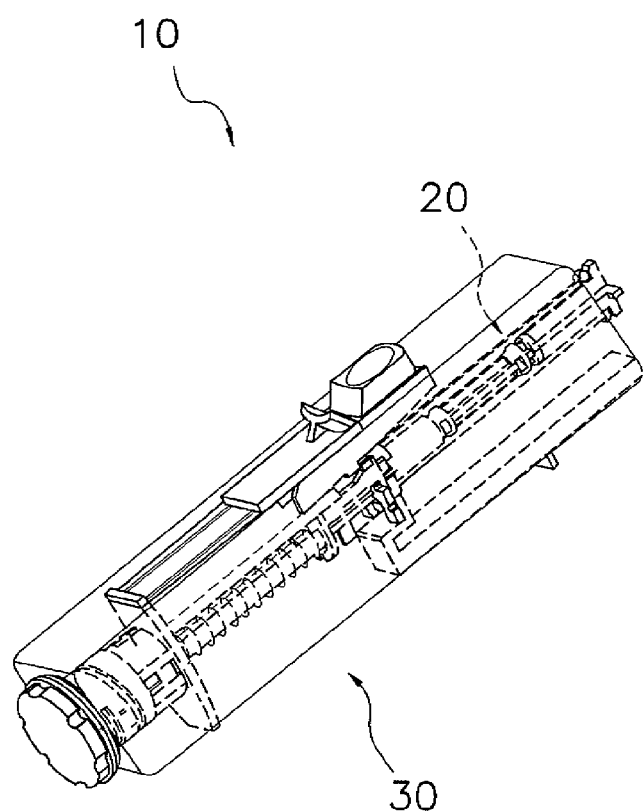
FIG. 1 is a perspective view illustrating appearance of a lancet device in accordance with an embodiment of the present invention.
Figure 2:
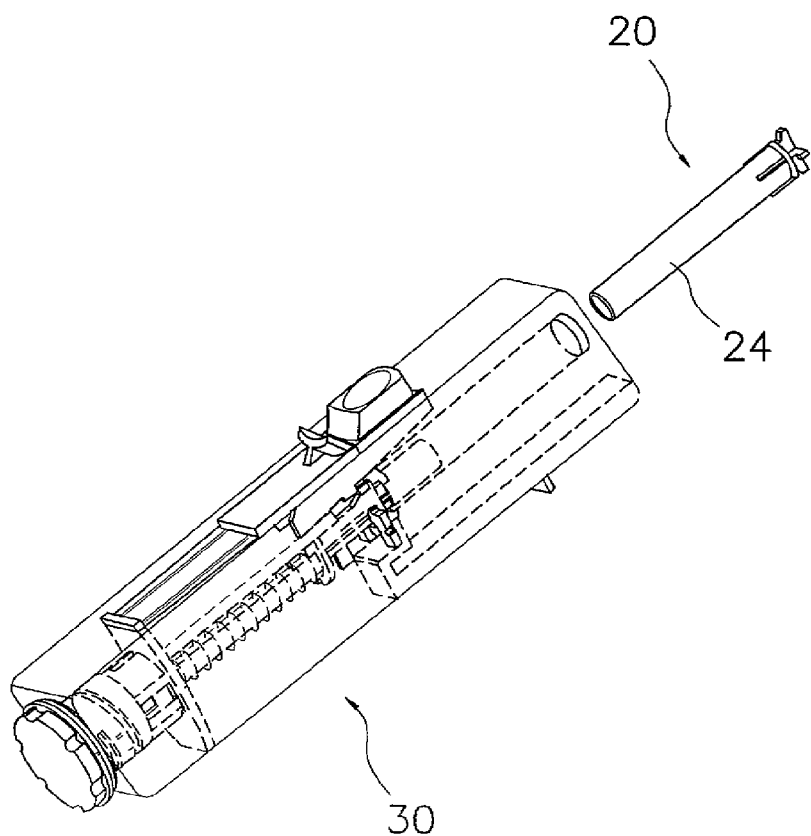
FIG. 2 is a perspective view illustrating a lancet and a main body, both of which make up the lancet device illustrated in FIG. 1.

Specifically, as illustrated in FIGS. 1 and 2, the lancet device 10 includes a lancet 20 and a main body 30.

The lancet 20 includes the stainless puncture needle 21 (see FIG. 4) for forming a puncture wound in the interior thereof, and as illustrated in FIG. 2, it is attached to the main body 30 from the front end side of the main body 30.

The main body 30 includes a coil spring 31 (see FIG. 6) for applying the urging force toward the puncture needle 21, and a return spring (not illustrated in the figures). The coil spring 31 applies the urging force for protruding the puncture needle 21 toward the front end side in a puncture direction. The return spring applies the opposite urging force from the urging force applied by the coil spring 31 in order to bring the puncture needle 21 shot by means of the coil spring 31 back into a housing 35.

Note that the term front end side•used in the following explanation means a side from which the tip of the puncture needle 21 of the lancet 20 to be described protrudes, and on the other hand, the term rear end side•means the opposite side from the front end side.

Configuration of Lancet 20

Figure 3:
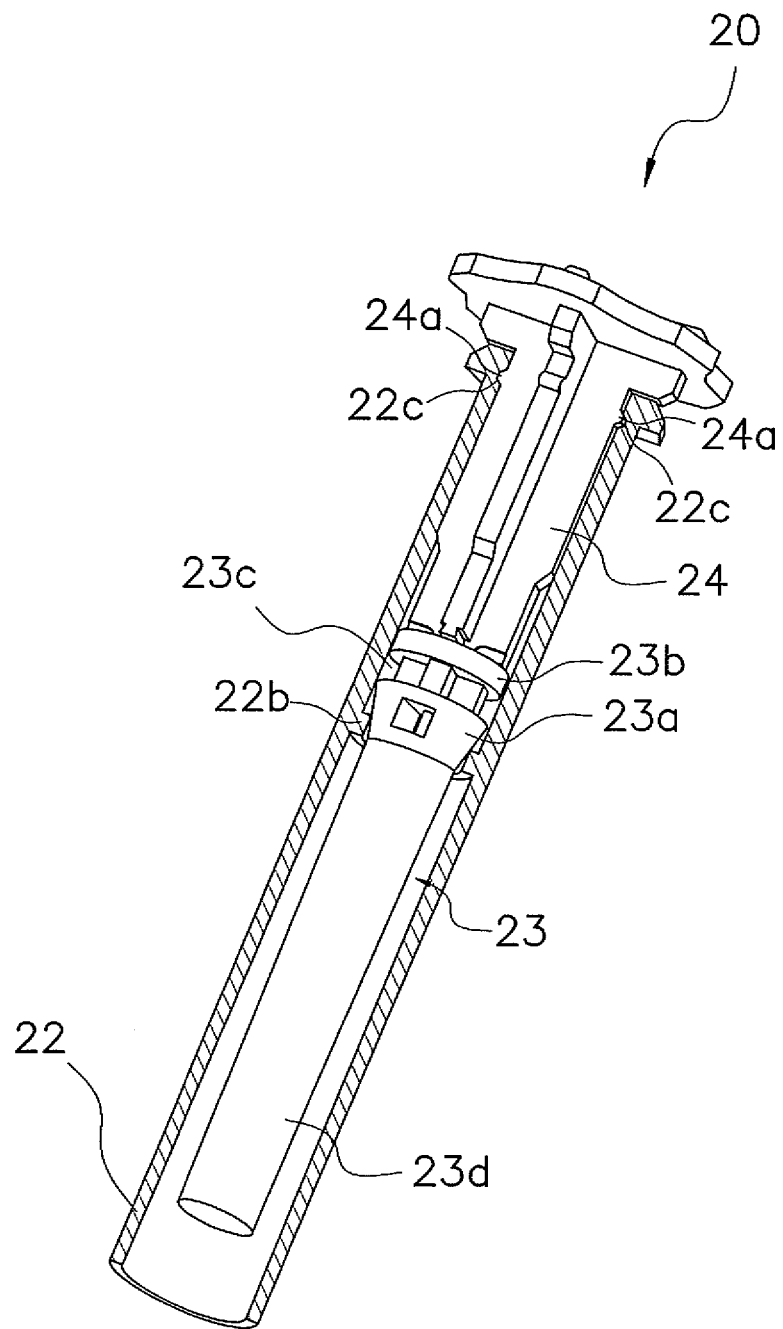
FIG. 3 is a partial cross-sectional view illustrating an interior configuration of a casing of the lancet included in the lancet device illustrated in FIG. 1.

As illustrated in FIG. 3, the lancet 20 includes an approximately cylindrical-shaped casing (casing member) 22, and a puncture body 23 that is accommodated in the casing 22 so that it is allowed to move in the front and rear end sides of the puncture direction when the lancet device 10 is used. Note that FIG. 3 illustrates a cross-sectional view of the casing 22 in order to conveniently explain the interior configuration of the approximately cylindrical-shaped casing 22.

Figure 4:
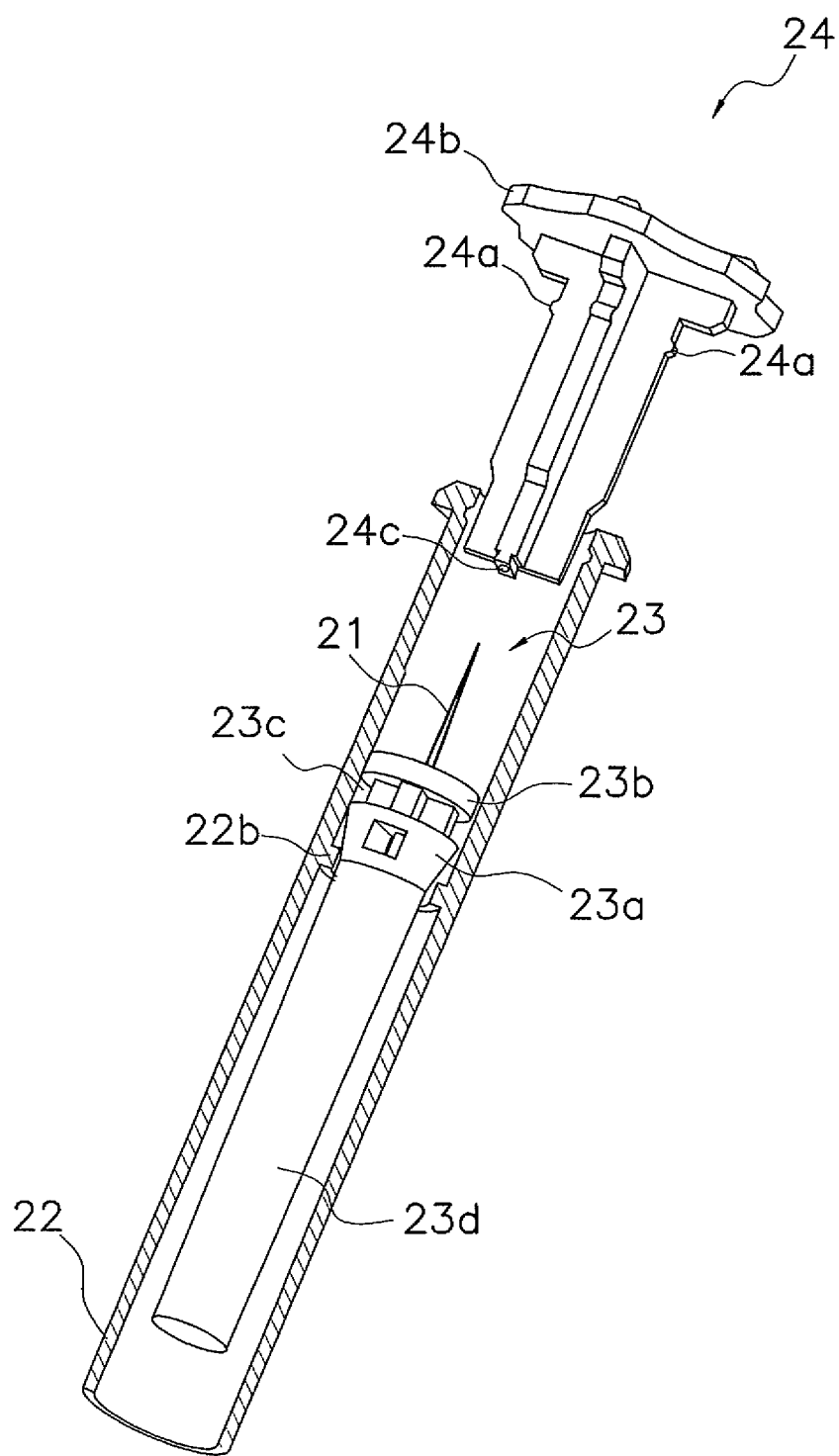
FIG. 4 is a perspective view illustrating a condition that a puncture body and a cap, both of which are included in the lancet illustrated in FIG. 2, are detached from each other.

The puncture body 23 is made of a resin such as PE (polyethylene) and is integrally formed with the puncture needle 21 for forming a puncture wound on the skin (see FIG. 4). As illustrated in FIG. 3, a taper portion 23a, a flange portion 23b, a groove (engaging portion) 23c, and an insertion portion 23d are formed in a portion of the puncture body 23 that is made of the resin. The taper portion 23a, the flange portion 23b, and the groove 23c are formed in the front end side from which the puncture needle 21 is exposed. The taper portion 23a is a member that is formed to taper toward the rear end side, and its cross-section perpendicular to the puncture direction is formed in an oval shape. The flange portion 23b is a disc-shaped member that is formed in the outmost of the front end side of the puncture body 23, and the puncture needle 21 protrudes from the center portion of the disc. The groove 23c is a concave formed to be interposed between the taper portion 23a and the flange portion 23b. After the puncture body 23 is used, it is moved to the rear end side relative to the casing 22, and a convex portion (engaging portion) 22b of the casing 22 to be described is engaged with the groove 23c. With this configuration, it is possible to prevent the puncture needle 21 from protruding from the casing 22 because the puncture body 23 is prevented from moving in the interior of the casing 22, and it is also possible to retain the puncture body 23 in the interior of the casing 22 (see FIG. 9). As illustrated in FIGS. 3 and 4, the insertion portion 23d is a member whose diameter in the puncture direction is uniformly formed, and is inserted into a mounting portion 32a of a puncture body holder (lancet holder) 32 of the main body 30 to be described. Here, the inner diameter of the cylindrical-shaped mounting portion 32a that is formed on the front end side (attachment side) of the puncture body holder 32 is approximately the same as the outer diameter of the insertion portion 23d to be inserted therein. Therefore, the puncture body 23 is retained in the mounting portion 32a of the puncture body holder 32 by the frictional force. Furthermore, when a fastening member 38 to be described fastens the outer peripheral portion of the mounting portion 32a of the puncture body holder 32 inwardly (in a direction intersectional to the puncture direction), the puncture body 23 is further tightly retained in the puncture body holder 32. With this configuration, it is possible to move the puncture body 23 back and forth in the puncture direction together with the puncture body holder 32 by means of the elastic force of the coil spring 31 disposed on the rear end side of the puncture body holder 32 in the main body 30.

In addition, as illustrated in FIGS. 3 and 4, a cap 24 is attached to the puncture needle 21 so as to cover the tip thereof, and thus it functions as a protection for preventing the tip of the puncture needle 21 from being exposed outside before the lancet 20 is used. The cap 24 is integrally formed with the puncture needle 21 as is the case with the puncture body 23, and a portion of the cap 24 is connected to the flange portion 23b of the puncture body 23. With this configuration, as illustrated in FIG. 4, when the lancet 20 is used, the cap 24 is twisted and pulled out, and accordingly the connected portion between the cap 24 and the flange portion 23b is disconnected. Thus, it is possible to expose the puncture needle 21 in the interior of the casing 22. In addition, the cap 24 includes a protruding portion 24a, a lid member 24b, and a hole 24c. The protruding portion 24a is a portion formed to protrude in a direction intersectional to the puncture direction, and as illustrated in FIG. 3, it is engaged with a groove 22c that is to be described and is formed in the end portion of the casing 22 on the front end side, while the cap 24 is being mounted to the casing 22. With this configuration, it is possible to retain the puncture body 23 in the interior of the casing 22 before the lancet 20 is used. The lid member 24b functions as a lid for covering the outmost front end portion of the casing 22 before the lancet 20 is used. The hole 24c is a hole that is formed on the tip side of the puncture needle 21 so as to closely make contact with the puncture needle 21 when the puncture needle 21, the puncture body 23, and the cap 24 are integrally formed, and the puncture needle 21 is being inserted in the hole 24c until the cap 24 is disconnected from the puncture body 23.

Figure 5:
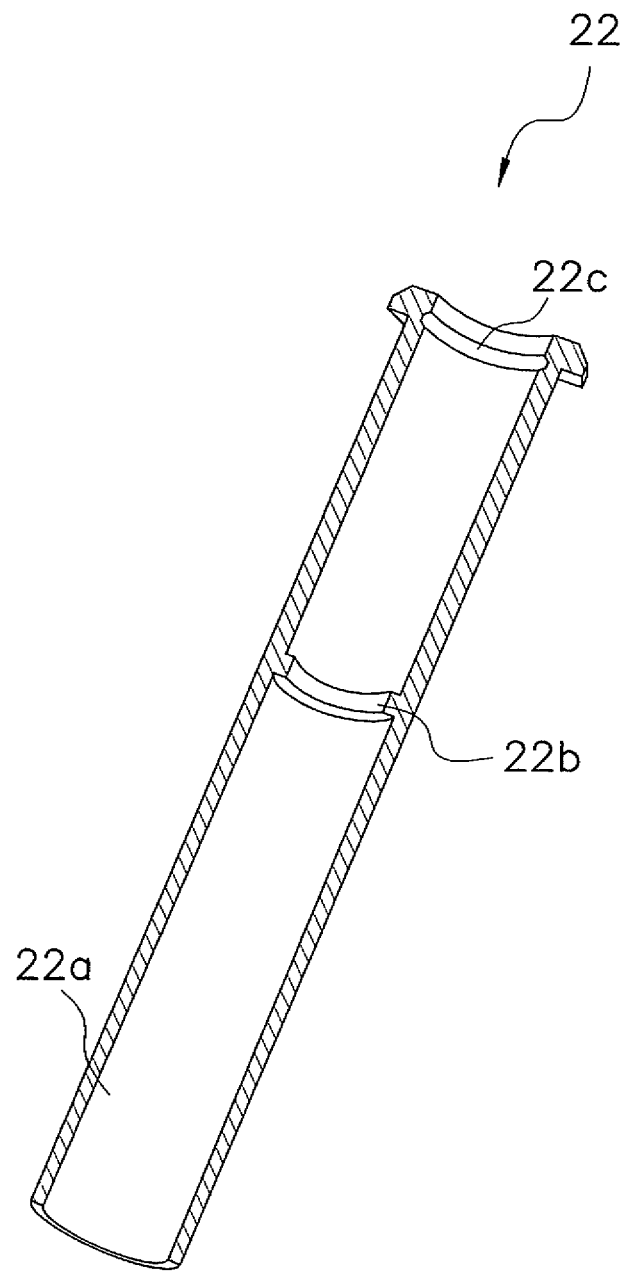
FIG. 5 is a cross-sectional view illustrating an interior configuration of a casing included in the lancet illustrated in FIG. 2.
Figure 8A:
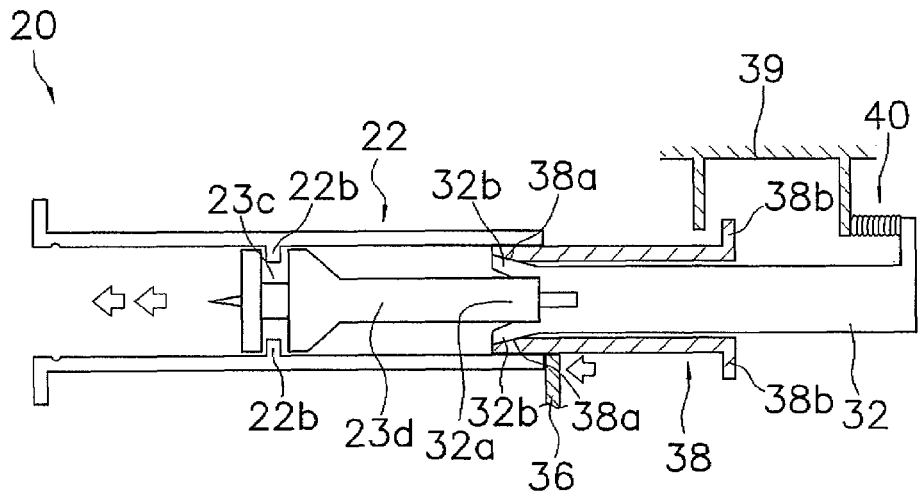
FIGS. 8(a) and 8(b) are sectional side views illustrating a condition that the lancet in FIG. 2 is detached from the main body side after use.
Figure 8B:
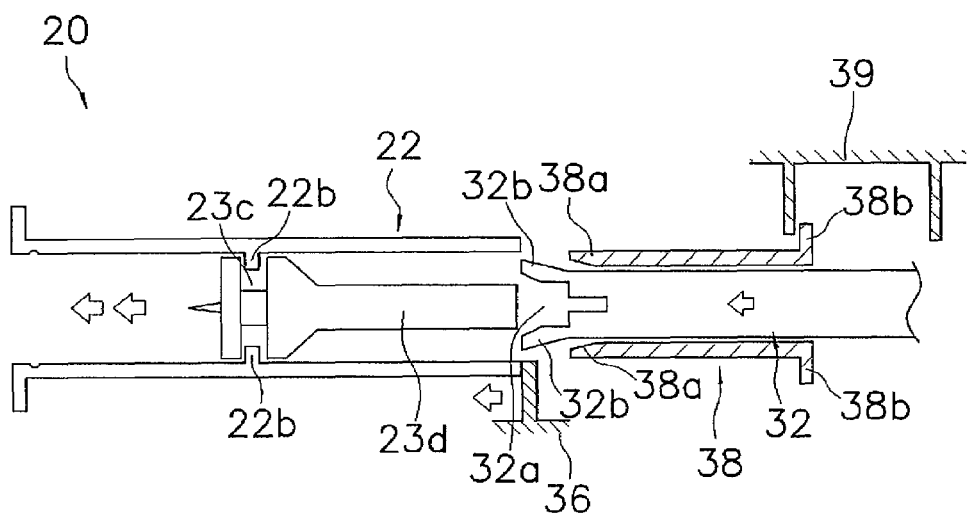

The casing 22 is an approximately cylindrical-shaped member, and accommodates the puncture body 23 in the interior thereof before use of the lancet 20 and continues to accommodate it in the interior thereof by the time when the lancet 20 is removed from the main body 30 side and is disposed after it is used. In addition, as illustrated in FIG. 5, the casing 22 includes an inner peripheral surface 22a, the convex portion 22b, and the groove 22c. The inner peripheral surface 22a is formed to have radius that is slightly larger than that of the taper portion 23a and the flange portion 23b of the puncture body 23. When the lancet 20 is used, the puncture body 23 moves in the front and rear end sides of the puncture direction. The convex portion 22b is a member that protrudes inwardly from the inner peripheral surface 22a of the casing 22, and is formed in the vicinity of the center portion of the casing 22 in the longitudinal direction. When the lancet 20 is disposed after it is used, the puncture body 23 is retracted to the rear end side, and as illustrated in FIGS. 8(a) and 8(b), the groove 23c of the puncture body 23 is engaged with the convex portion 22b. With this configuration, it is possible to prevent the puncture needle 21 from protruding from the front end of the casing 22 after the lancet 20 is used, and thus it is possible to ensure safety after the lancet 20 is used. The groove 22c is a concave that is formed on the inner peripheral surface 22a of the casing 22 on the front end side. The protruding portion 24a of the cap 24 is engaged with the groove 22c before the lancet 20 is used. Therefore, it is possible to retain the puncture body 23 in the interior of the casing 22 so that the puncture body 23 is not allowed to move in the front and rear end sides in the puncture direction.

Configuration of Main Body 30

Figure 6:
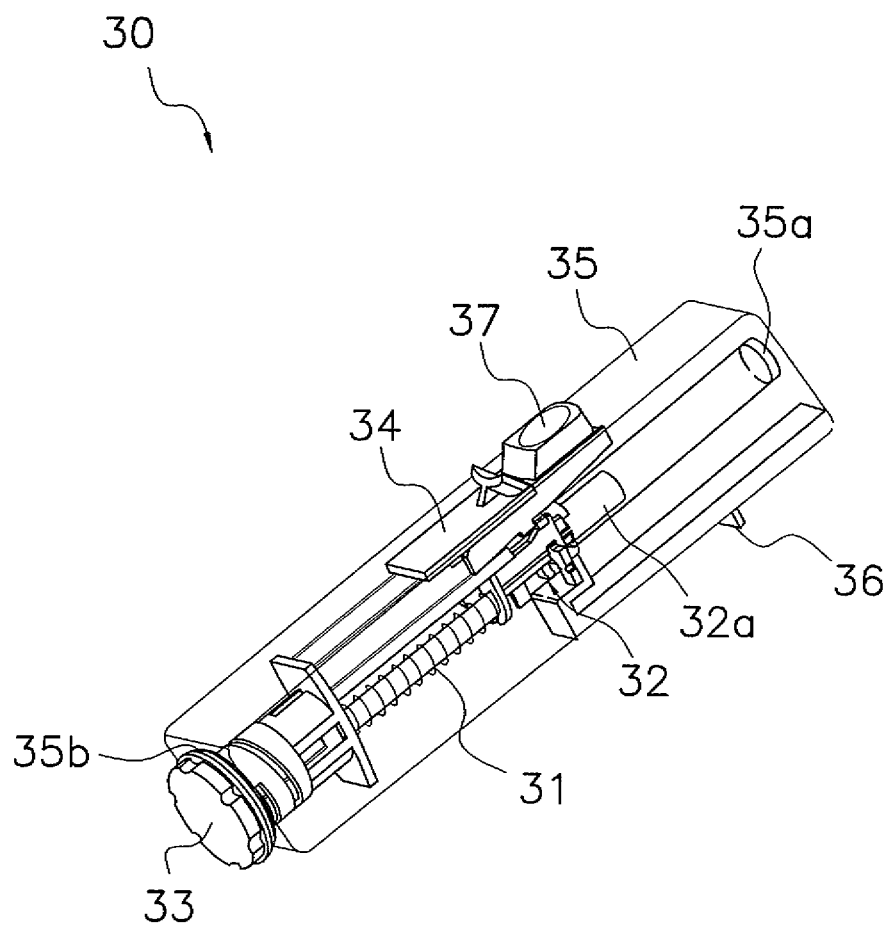
FIG. 6 is a perspective view illustrating a configuration of a main body included in the lancet device illustrated in FIG. 1.

As illustrated in FIG. 6, the main body 30 includes the coil spring 31, the puncture body holder 32, a rotator 33, an urging member 34, the housing 35, a removing portion 36, a setting-release button 37, and the fastening member 38 (see e.g., FIG. 7(*a*)), and the above described lancet 20 is attached to the main body 30 from the front end side thereof (see FIG. 2).

The coil spring 31 is a member that applies the urging force for moving the puncture body 23 of the lancet 20 in the puncture direction, and is disposed on the rear end side of the puncture body holder 32 so as to abut to the puncture body holder 32. With this configuration, when a cocked state is produced by pulling the urging member 34 back to the rear end side, the coil spring 31 is compressed, and thus stores the energy for shooting the puncture needle 21.

The return spring is a member that applies the urging force for bringing the puncture body 23 of the lancet 20 back to the interior of the casing 22 after the puncture body 23 of the lancet 20 is protruded from the front end of the casing 22 by means of the coil spring 31, and is disposed in the inner side of the coil spring 31. Specifically, when the puncture needle 21 is shot toward the front end side by means of the above described coil spring 31, the puncture body holder 32 is moved to the front end side. Thus, the return spring's state is changed from a stationary state in which the return spring is not loaded to a state in which the return spring is compressed while a contact position that the return spring makes contact with the urging member 34 functions as a support position. Therefore, the urging force (spring force) for changing the return spring's state from the compressed state to the original stationary state is generated in the return spring, and thus the puncture needle 21 is brought back to the rear end side together with the puncture body holder 32 by the force. In addition, a spring whose elastic force is smaller than that of the coil spring 31 is used as the return spring. With this configuration, even when the coil spring 31 and the return spring apply the opposite urging forces (spring forces) from each other, it is possible to smoothly perform a puncture without weakening the force and the speed of the puncture body 23 when it is shot by means of the coil spring 31.

The puncture body holder 32 is molded with a resin such as PE as is the case with the puncture body 23, and retains a rear end side portion of the lancet 20 (an insertion portion 23*d*), which is inserted from a puncture hole 35*a* formed in the front end of the housing 35, in the mounting portion 32*a* (see FIGS. 7(*a*) and 7(*b*)). In addition, the mounting portion 32*a* of the puncture body holder 32 has the inner diameter that is approximately the same as the outer diameter of the insertion portion 23*d* of the puncture body 23. Therefore, when the insertion portion 23*d* with the uniform diameter is inserted in the mounting portion 32*a*, the frictional force is generated between the inner peripheral portion of the mounting portion 32*a* of the puncture body holder 32 and the outer peripheral portion of the insertion portion 23*d*. Then, the puncture body 23 is retained in the puncture body holder 32 by means of the frictional force. In addition, not only the above described frictional force, but also the force for retaining the insertion portion 23*d* by fastening the insertion portion 23*d* from the outer peripheral surface side when the fastening member 38 to be described makes contact with the outer peripheral surface of the mounting portion 32*a* of the puncture body holder 32, is added as the force for retaining the insertion portion 23*d* of the puncture body 23 in the mounting portion 32*a* of the puncture body holder 32. Here, when the cap 24 is removed while the lancet 20 is being attached to the main body 30, the engaged state between the cap 24 and the casing 22 is released first. This is because the engaging force between the cap 24 and the casing 22 is smaller than that between the casing 22 and the housing 35, and the coupling force between the cap 24 and the puncture needle 21 and that between the cap 24 and the puncture body 23 are smaller than the retaining force for retaining the puncture body 23 in the puncture body holder 32. As a result, even when the cap 24 is pulled out of the casing 22, cap 24 is allowed to be removed without releasing the engaged state between the puncture body 23 and the puncture body holder 32. In addition, a taper portion 32*b* is formed in the tip of the mounting portion 32*a* of the puncture body holder 32, and the inner and outer diameters thereof are formed to be larger toward the front end side. Furthermore, a portion of the taper portion 32*b* with the smallest inner diameter is formed to be approximately the same as the outer diameter of the insertion portion 23*d* of the puncture body 23. Therefore, when the puncture body 23 is attached to the puncture body holder 32, it is possible to guide the insertion portion 23*d* into the mounting portion 32*a* by the taper portion 32*b*. Furthermore, the outer diameter of the taper portion 32*b* is formed to be larger toward the front end portion side.

Note that the two-phased retaining force for retaining the puncture body 23 in the mounting portion 32*a* of the puncture body holder 32 will be hereinafter described in detail.

The rotator 33 rotates around the axial direction in the circumferential direction when the externally exposed dial portion thereof is rotated. The rotator 33 includes a spiral-shaped rib that is formed on the inner surface of the cylindrical portion of the dial portion on the front end side. A convex portion (not illustrated in the figures) that is formed on the end portion of the puncture body holder 32 on the rear end side makes contact with the rib when the puncture body holder 32 is urged toward the front end side by the elastic force of the coil spring 31, and thus the amount that the puncture body holder 32 moves is regulated. Therefore, when the position that the convex portion and the rib make contact with each other is changed by rotating the rotator 33, it is possible to regulate the amount that the puncture body holder 32 moves. As a result, it is possible to regulate the position of the puncture body 23 back and force in the puncture direction, and accordingly, it is possible to control the depth of a puncture by regulating the amount of protrusion of the puncture needle 21 by rotating the rotator 33 before a puncture wound is formed on the skin.

The urging member 34 is a member for storing the energy of shooting the puncture needle 21 by compressing the coil spring 31 when the puncture body 23 is shot again after the lancet 20 is attached and the puncture needle 21 is shot in the puncture direction, and is exposed to the lateral surface of the housing 35. It is possible to set the puncture needle 21 to be ready to be shot when a cocked state is produced by pulling the urging member 34 back to the rear end side and moving the puncture body holder 32 to the rear end side.

The housing 35 accommodates the above described members such as the coil spring 31, the return spring, and the puncture body holder 32, and forms a framework of the lancet device 10. In addition, as illustrated in FIG. 6, the housing 35 includes the puncture hole 35*a* in an end portion thereof on the front end side, and also includes an opening 35*b* in which the rotator 33 is accommodated in an end portion thereof on the rear end side. The lancet 20 is inserted into the puncture hole 35*a*, and the tip of the puncture needle 21 is shot out of the opening of the casing 22 of the lancet 20 when a puncture is performed. The opening 35*b* is formed in a circular shape so as to be matched with the shape of the rotator 33.

The removing portion 36 is exposed to a side of the approximately rectangular solid housing 35, and this side is opposed to the side to which the urging member 34 is exposed. In addition, the removing portion 36 is disposed in the interior of the housing 35 so as to make contact with the end portion of the casing 22 on the rear end side. When the removing portion 36 is moved to the front end side after a puncture is performed, the position of the puncture body holder 32 in the puncture direction is kept by means of the elastic force of an elastic member 40 (see FIG. 8(a)). Next, when only the casing 22 is moved to the front end side, the convex portion 22b of the casing 22 and the groove 23c of the puncture body 23 are allowed to be engaged with each other. Here, when the removing portion 36 is further moved forward, the puncture body 23 moves to the front end side together with the puncture body holder 32 including the fastening member 38 while the puncture body 23 acts against the elastic force of the above described elastic member 40. This is because the puncture body 23 is tightly retained in the puncture body holder 32. Here, a convex portion 38b that is formed on an end portion of the fastening member 38 on the rear end side makes contact with a portion of a retaining abutment 39. Thus, the fastening member 38 moves to the rear end side relative to the puncture body holder 32. With this configuration, the engaged state between the inner peripheral surface of the fastening member 38 and the outer peripheral surface of the puncture body holder 32 is released, and accordingly the fastened state is also released. As a result, it is possible to relatively easily release a retained state of the puncture body 23 (insertion portion 23d) in the mounting portion 32a of the puncture body holder 32, and accordingly it is possible to remove the lancet 20 from the main body 30.

The setting-release button 37 is a member for releasing a standby state that the puncture needle 21, which is cocked when the lancet 20 is attached, or which is cocked again by the urging member 34 after the lancet 20 is attached and is then shot, is allowed to be shot. The setting-release button 37 is also exposed to the outside of the housing 35. Therefore, when a puncture is performed, the puncture needle 21 is shot in the puncture direction by releasing the cocked state between a notch portion of the puncture body holder 32 and that of the housing 35 when the setting-release button 37 is pressed after the puncture needle 21 is set to be ready to be shot as described above.

The fastening member 38 is made of a resin such as POM, and is provided along the outer periphery of the puncture body holder 32 in the interior of the main body 30. Then, the fastening member 38 includes an abutment 38a on the front end side in the puncture direction, and also includes the convex portion 38b on the rear end side in the puncture direction. The inner diameter of the abutment 38a is formed to be larger toward the front end side so as to match the shape of the above described taper portion 32b of the puncture body holder 32. When the abutment 38a of the puncture body holder 32 makes contact with and moves along the taper portion 32b, the puncture body 23 is fastened in the puncture body holder 32. The convex portion 38b makes contact with the retaining abutment 39 that is provided lateral to the fastening member 38 when the puncture body 23 is fastened or unfastened.

Explanation of Operation of Lancet Device 10

Figure 7A:
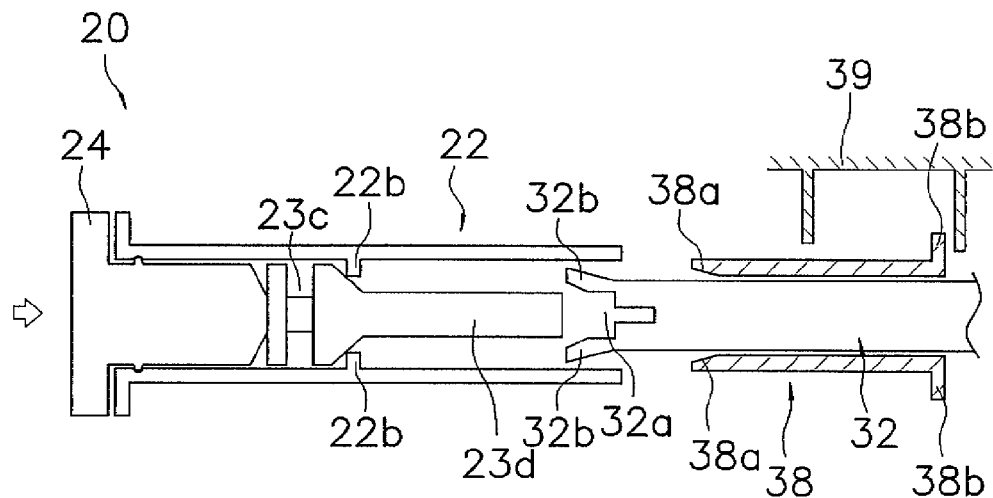
FIGS. 7(a) and 7(b) are sectional side views illustrating a condition that the lancet in FIG. 2 is attached to a puncture body holder on the main body side.
Figure 7B:
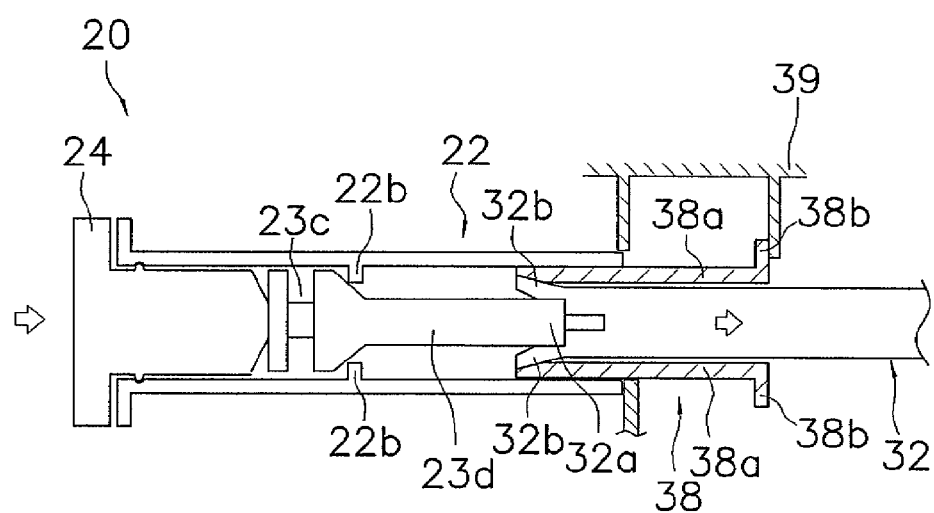

As illustrated in FIG. 2, when the lancet device 10 of the present embodiment is started to be used, an unused new lancet 20 is firstly inserted into the puncture hole 35a (see FIG. 6) of the main body 30. As illustrated in FIG. 7(a), when the lancet 20 is inserted into the rearward of the puncture hole 35a, the insertion portion 23d illustrated in FIG. 3, which is formed in the end portion of the puncture body 23 on the rear end side, is inserted into the cylindrical-shaped mounting portion 32a of the puncture body holder 32. Here, the puncture body 23 is retained in the mounting portion 32a by means of the frictional force, because the outer diameter of the insertion portion 23d of the puncture body 23 and the inner diameter of the mounting portion 32a of the puncture body holder 32 are formed in approximately the same size. Note that the frictional force is generated between the insertion portion 23d of the puncture body 23 and the mounting portion 32a of the puncture body holder 32. However, the puncture body holder 32 does not move back because the puncture body holder 32 is urged to the front end side in the puncture direction by means of the coil spring 31. Then, as illustrated in FIG. 7(b), when the puncture body 23 is further pressed into the rear end side from the position where the insertion portion 23d is being inserted into the rearward of the mounting portion 32a, the outer peripheral portion of the taper portion 32b of the puncture body holder 32 makes contact with the inner peripheral portion of the fastening member 38. Here, as illustrated in FIG. 7(b), the convex portion 38b that is formed in the end portion of the fastening member 38 on the rear end side makes contact with a portion of the retaining abutment 39, and thus the convex portion 38b is regulated not to move further. Accordingly, the puncture body holder 32 moves to the rear end side relative to the fastening member 38. With this configuration, it is possible to make the taper portion 32b formed in the front end side of the mounting portion 32a of the puncture body holder 32 reliably contact with the abutment 38a formed in the inner peripheral portion of the fastening member 38. Note that the state that the fastening member 38 makes contact with the puncture body holder 32 is kept even when the state that the retaining abutment 39 makes contact with the fastening member 38 is released by means of the frictional force generated when the puncture body holder 32 is fastened by the fastening member 38. Furthermore, the outer diameter of the taper portion 32b is formed to be larger toward the front end side from the rear end side. Therefore, it is possible to tightly retain the puncture body 23 in the mounting portion 32a of the puncture body holder 32 by inwardly fastening the mounting portion 32a as a result of moving the puncture body holder 32 to the rear end side relative to the fastening member 38. Then, when the lancet 20 is further inserted into the rearward, the lancet 20 is completely mounted to the main body 30. At the same time as this, the lancet 20 is cocked and is set to be in a standby state that the puncture needle 21 is ready to be shot.

Next, the cap 24 that is integrally formed with the puncture body 23 is removed to expose the puncture needle 21 (see FIG. 4). A portion of the cap 24 is connected to a surface of the flange portion 23b of the puncture body 23 on the front end side. Therefore, the cap 24 is removed when the connected portion is torsionally-sheared by rotating the cap 24. Here, the pulling force to the front end side is applied for the cap 24 to be removed. Therefore, the pulling force to the front end side is also applied to the puncture body 23, a portion of which is connected to the cap 24. However, as illustrated in FIG. 7(b), when the cap 24 is removed, the end portion (insertion portion 23d) of the puncture body 23 on the rear end side is tightly retained in the mounting portion 32a of the puncture body holder 32. In addition, the retaining force for retaining the puncture body 23 in the puncture body holder 32 is larger than the force necessary to detach the cap 24 from the puncture body 23. As a result, even when the cap 24 is removed from the casing 22, the puncture body 23 is not detached from the puncture body holder 32 together with the cap 24. Note that when the puncture body 23 with which a puncture has been once performed is shot again, the puncture body 23 may be cocked with the urging member 34 and the urging force may be applied by compressing the coil spring 31, and then the cocked state may be released by the setting-release button 37 while this state is kept.

Next, when the standby state is released by pressing the setting-release button 37 while the puncture hole 35a makes contact with an affected part (e.g., the skin of a finger) for which a puncture is performed, the tip of the puncture needle 21, which has a predetermined length, protrudes from the puncture hole 35a formed in the main body 30 on the outermost front end side. Then, the puncture needle 21 is brought back to the casing 22 again by means of the spring force of the return spring (not illustrated in the figures) immediately after a puncture is performed. Note that the movable range of the puncture needle 21 immediately after the puncture is performed corresponds to a range between the standby position illustrated in FIG. 4 of the puncture body 23 before it is shot and the puncture position in which the tip of the puncture needle 21 protrudes by a few millimeters.

After the puncture is completed, the lancet 20 is removed from the main body 30 by means of the removing portion 36, and is then disposed. Removal of the lancet 20 from the main body 30 is performed by means of the removing portion 36 illustrated in FIG. 6. Specifically, when the removing portion 36 is moved to the front end side, only the casing 22 is firstly moved to the front end side. Accordingly, the puncture body 23 that is being retained in the puncture body holder 32 is moved to the rear end side relative to the casing 22. Here, the taper portion 23a that is formed in the vicinity of the center portion of the puncture body 23 is moved while it presses and enlarges a part around the convex portion 22b formed on the inner peripheral surface 22a of the casing 22, and thus the convex portion 22b of the casing 22 is engaged with the groove 23c of the puncture body 23 (see FIG. 9). This engaged state is tightly formed, and therefore this makes it possible to prevent the tip of the puncture needle 21 from protruding from the front end side of the casing 22 after the lancet 20 is removed from the main body 30. With this configuration, the puncture needle 21 is prevented from protruding with the cap 24 before the lancet 20 is used, and the puncture body 23 is retained in the casing 22 by means of the engaged state with large engagement force after the lancet 20 is used. Therefore, it is possible to avoid danger that may be generated before and after the lancet 20 is used.

Next, as illustrated in FIG. 8(b), when the removing portion 36 is further pressed after the convex portion 22b of the casing 22 is engaged with the groove 23c of the puncture body 23, a state that the puncture body 23 is retained in the puncture body holder 32 is released. Specifically, the above described engaging force between the convex portion 22b of the casing 22 and the groove 23c of the puncture body 23 is larger than the retaining force for retaining the puncture body 23 in the puncture body holder 32. Therefore, when the removing portion 36 is further pressed to the front end side in this engaged state, the puncture body holder 32 is moved to the front end side together with the fastening member 38 when the puncture body 23 is moved to the front end side. This is because the puncture body 23 is tightly retained in the puncture body holder 32. Here, the convex portion 38b that is formed in the end portion of the fastening member 38 on the rear end side makes contact with a portion of the retaining abutment 39. Because of this, when the removing portion 36 is further pressed to the front end side from the position where the convex portion 38b makes contact with a portion of the retaining abutment 39 (see FIG. 8(a)), the puncture body holder 32 is moved to the front end side relative to the fastening member 38. With this configuration, as illustrated in FIG. 8(b), a state that the inner peripheral surface of the fastening member 38 and the outer peripheral surface of the taper portion 32b of the puncture body holder 32 make contact with each other is released, and accordingly, it is possible to release the fastened state in the mounting portion 32a. Also, in a state illustrated in FIG. 8(b), the frictional force generated between the mounting portion 32a and the insertion portion 23d is only left as the retaining force for retaining the insertion portion 23d in the mounting portion 32a of the puncture body holder 32. Because of this, it is possible to relatively easily release a state that the puncture body 23 is retained in the puncture body holder 32 and remove the lancet 20 from the main body 30 side by further pressing the removing portion 36 to the front end side in the state illustrated in FIG. 8(b).

Figure 9:
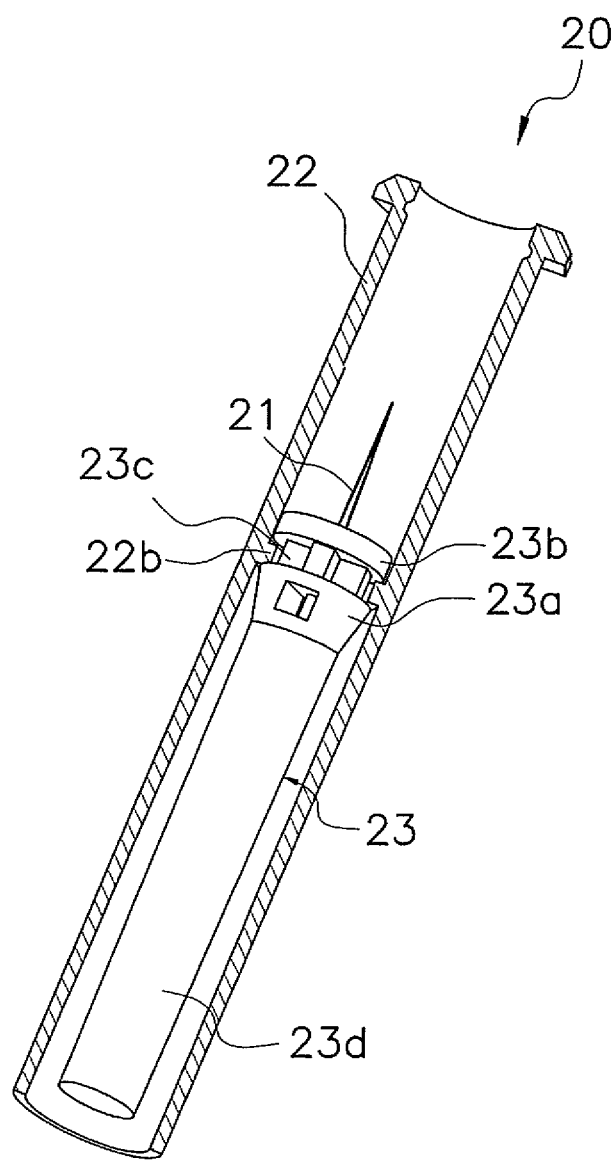
FIG. 9 is a sectional side view illustrating a condition that the puncture body and the casing in FIG. 8 are engaged with each other.

With the above described procedure, the used lancet 20 is removed from the main body 30 and is disposed. Here, as illustrated in FIG. 9, the puncture body 23 is tightly retained in the casing 22 by means of the engagement force in the removed lancet 20. Therefore, it is possible to reliably prevent such cases that a user is injured by the tip of the puncture needle 21 protruded from the casing 22 and that a user is infected by a disease through a fluid or the like attaching to the puncture needle 21. Furthermore, in the lancet 20 that has once been removed from the main body 30, the casing 22 and the puncture body 23 are engaged with reach other such that the puncture body 23 is retained in the casing 22. Therefore, this makes it difficult to reuse the lancet 20, compared to the conventional lancets.

Features of Lancet Device 10 of Present Embodiment (1)

The lancet device 10 in accordance with the present embodiment is a lancet device configured to perform a puncture by applying the urging force to the puncture body holder 32 in the frontward of the puncture direction while the lancet 20 including the puncture needle 21 is attached to the tip (mounting portion 32a) of the puncture body holder 32. In addition, as illustrated in FIGS. 7(a) and 7(b), in the lancet device 10, the insertion portion 23d of the puncture body 23 that is inserted into the mounting portion 32a of the puncture body holder 32 is retained by means of the frictional force. Furthermore, when the fastening member 38 provided in the main body 30 side is moved in the puncture direction relative to the puncture body holder 32, it makes contact with the outer peripheral portion of the mounting portion 32a of the puncture body holder 32 and inwardly fastens the mounting portion 32a.

With this configuration, the puncture body 23 is retained in the puncture body holder 32 side by adding the retaining force, which is generated when a part around the mounting portion 32a of the puncture body holder 32 is fastened by the fastening member 38, to the retaining force by means of friction generated between the inner peripheral surface of the puncture body holder 32 and the outer peripheral surface of the puncture body 23. Accordingly, it is possible to achieve the lancet device 10 that has the strengthened retaining force for retaining the puncture body 23, compared to the conventional lancet devices. In addition, the lancet device 10 has a simple configuration that only the fastening member 38, which is relatively moved with the puncture body holder 32 and makes contact with the taper portion 32b formed in the tip side of the puncture body holder 32, is additionally provided for the lancet device 10. Accordingly, it is possible to provide the safer lancet device 10 without increasing the manufacturing cost.

(2)

As illustrated in the figures such as FIG. 7(b), in the lancet device 10 in accordance with the present embodiment, the insertion portion 23d of the puncture body 23 that is mounted to the tip of the puncture body holder 32, and the mounting portion 32a of the puncture body holder 32 are formed so that the outer diameter of the insertion portion 23d and the inner diameter of the mounting portion 32a are formed in approximately the same dimension.

With this configuration, it is possible to ensure the retaining force for simply retaining the puncture body 23 in the puncture body holder 32 by means of the frictional force generated between the mounting portion 32a of the puncture body holder 32 and the insertion portion 23d of the puncture body 23 only by inserting the insertion portion 23d into the mounting portion 32a before a fastened state is produced by the fastening member 38.

(3)

As illustrated in the FIGS. 7(a) and 7(b), when the lancet 20 is mounted to the main body 30 side in the lancet device 10 in accordance with the present embodiment, the insertion portion 23d of the puncture body 23 of the lancet 20 is inserted into the mounting portion 32a of the puncture body holder 32, and then the puncture body 23 is further pressed. Accordingly, the puncture body holder 32 is moved to the rear side in the puncture direction relative to the fastening member 38, and the fastening member 38 and the outer peripheral surface of the mounting portion 32a of the puncture body holder 32 are made contact with each other.

With this configuration, it is possible to produce a fastened state while the fastening member 38 and the puncture body holder 32 are made contact with each other in a series of operation performed when the lancet 20 is mounted to the main body 30 side. As a result, it is possible to enhance operability of the lancet 20 when it is mounted to the main body 30, and it is also possible to achieve the lancet device 10 that makes it possible to easily ensure sufficient retaining force.

(4)

In the lancet device 10 in accordance with the present embodiment, when the lancet 20 is removed from the main body 30 side after it is used, a fastened state for the puncture body holder 32 is released by moving the puncture body holder 32 to the front side in the puncture direction relative to the fastening member 38.

With this configuration, it is possible to smoothly move the puncture body holder 32 to the front side in the puncture direction relative to the fastening member 38 in a step of moving the puncture body holder 32 in an opposite direction from the direction in which the lancet 20 is mounted. As a result, it is possible to enhance operability of removing the lancet 20 from the main body 30 side, and it is also possible to easily pull the puncture body 23 retained only by the frictional force from the puncture body holder 32 after the fastened state of the puncture body holder 32 is released.

(5)

As illustrated in figures such as FIG. 7(a), in the lancet device 10 in accordance with the present embodiment, the taper portion 32b whose outer diameter is formed to be larger toward the front side from the rear side in the puncture direction is formed in the end portion of the mounting portion 32a of the puncture body holder 32 on the front end side in the puncture direction.

With this configuration, when the puncture body holder 32 is moved back relative to the fastening member 38, the outer peripheral surface of the taper portion 32b that is formed in the tip of the mounting portion 32a of the puncture body holder 32 makes contact with the inner peripheral surface of the fastening member 38. Here, the taper portion 32b is formed to have the outer diameter that becomes larger toward the front end side. Therefore, when the puncture body holder 32 is moved back relative to the fastening member 38, it is possible to inwardly fasten the mounting portion 32a from the outer peripheral surface side. As a result, it is possible to achieve the lancet device 10 that is capable of ensuring the sufficient retaining force with a simple configuration in which only the shape of the portion that the puncture body holder 32 and the fastening member 38 make contact with each other is devised.

(6)

As illustrated in the figures such as FIG. 7(b), in the lancet device 10 in accordance with the present embodiment, the mounting portion 32a is elastically deformed inwardly when the fastening member 38 makes contact with the outer peripheral surface of the mounting portion 32a of the puncture body holder 32.

With this configuration, it is possible to retain the puncture body 23 in the puncture body holder 32 side by means of the sufficient fastening force when the puncture body holder 32 is fastened. In addition, it is also possible to easily pull the puncture body 23 from the puncture body holder 32 by restoring the shape of the portion of the mounting portion 32a that has elastically been deformed when the fastened state of the puncture body holder 32 is released. As a result, it is possible to ensure the strong retaining force in the puncture body holder 32 only when necessary.

(7)

As illustrated in the figures such as FIG. 7(a), in the lancet device 10 in accordance with the present embodiment, the insertion portion 23d of the puncture body 23 that is inserted into the mounting portion 32a of the puncture body holder 32 is formed to have a uniform diameter in the puncture direction.

In general, when this type of insertion portion with the uniform diameter is inserted into the mounting portion of the puncture body holder, the puncture body 23 is retained in the puncture body holder 32 only by means of the frictional force. Therefore, it is impossible to retain the puncture body 23 in the puncture body holder 32 with sufficient retaining force.

According to the lancet device 10 of the present embodiment, it is possible to ensure the strong retaining force by the fastening force applied by the fastening member 38 in addition to the frictional force generated between the puncture body 23 and the puncture body holder 32. Accordingly, even when the diameter of the insertion portion 23d of the puncture body 23 is uniformly formed in the puncture direction, it is possible to ensure the sufficient retaining force.

Alternative Embodiments

An embodiment of the present invention has been explained above. However, the present invention is not limited to the above described embodiment, and a variety of changes may be made without departing from the scope of the invention.

(A)

In the above described embodiment, an example is explained that the outer diameter of the insertion portion 23d of the puncture body 23 and the inner diameter of the mounting portion 32a of the puncture body holder 32 are formed in approximately the same size and the puncture body 23 is retained in the puncture body holder 32 by means of the frictional force generated between the puncture body 23 and the puncture body holder 32. However, the present invention is not limited to this configuration.

For example, a configuration may be provided that the inner diameter of the mounting portion of the puncture body holder is formed to be larger than the outer diameter of the insertion portion of the puncture body and the frictional force is not generated between the puncture body and the mounting portion only by inserting the puncture body into the mounting portion. With this configuration, the same effect as the above described effect is achieved that it is possible to tightly retain the puncture body by inwardly fastening the mounting portion of the puncture body holder by means of the fastening member.

(B)

In the above described embodiment, an example is explained that the puncture body holder 32 and the fastening member 38 are separately formed. However, the present invention is not limited to this configuration.

Figure 10A:
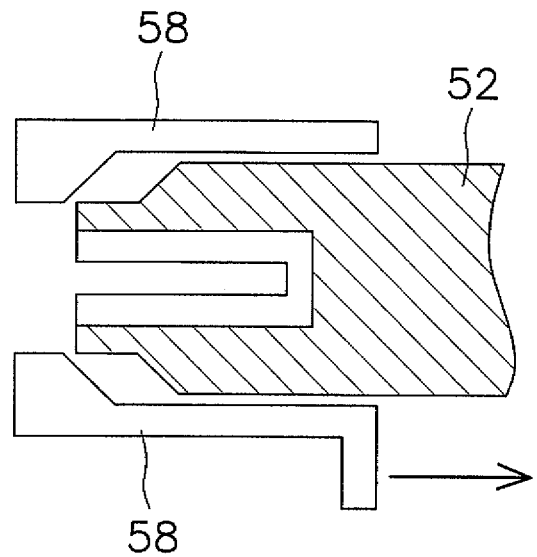
FIGS. 10(a) and 10(b) are sectional side views illustrating conditions of a puncture body holder of a puncture body included in a lancet in accordance with other embodiment of the present invention before and after fastened, respectively.
Figure 10B:
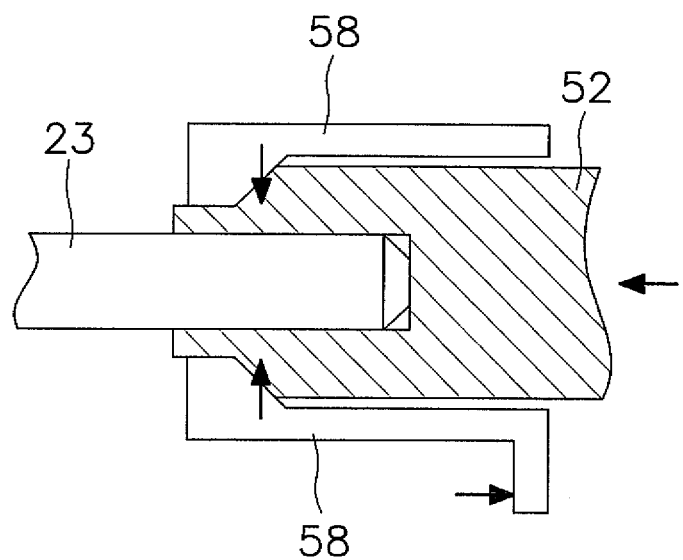

For example, members 52 and 58 illustrated in FIGS. 10(a) and 10(b) may be used as members forming a part of the puncture body holder. In other words, the puncture body holder may be divided into a holder portion and a fastening portion.

(C)

In the above described embodiment, an example is explained that the puncture body holder 32 is fastened by moving the puncture body holder 32 in the puncture direction with respect to the fastening member 38. However, the present invention is not limited to this configuration.

For example, the puncture body holder may be fastened by interlocking the convex portion formed on the outer peripheral surface of the puncture body holder with the concave portion formed on the inner peripheral surface of the fastening member, and then by rotating the puncture body holder with respect to the fastening member or by rotating the fastening member with respect to the puncture body holder.

Also, the puncture body holder may be fastened by forming the cross-section of the puncture body holder in an oval shape and forming the cross-section of the fastening member on the inner diameter side in a circular shape or an oval shape whose diameter is shorter than the longer diameter of the oval-shaped cross-section of the puncture body holder, and then by rotating the puncture body holder with respect to the fastening member or by rotating the fastening member with respect to the puncture body holder.

Furthermore, the puncture body holder may be fastened by interlocking a plurality of convex portions formed on the outer peripheral surface of the puncture body holder at a small pitch with a plurality of concave portions formed on the inner peripheral surface of the fastening member at the same pitch as that of the convex portions, and then by rotating the puncture body holder with respect to the fastening member or by rotating the fastening member with respect to the puncture body holder.

Also, the puncture body holder may be fastened by forming the cross-section of the puncture body holder in a polygon (e.g., equilateral octagon) and by rotating any of the members so as to make contact with the shape of the fastening member on the inner diameter side.

(D)

As illustrated in FIGS. 7(a) and 7(b), in the above described embodiment, an example is explained that the puncture body holder 32 is fastened by moving the puncture body holder 32 to the rear side in the puncture direction relative to the fastening member 38. However, the present invention is not limited to this configuration.

For example, as illustrated in FIGS. 10(a) and 10(b), a configuration may be provided that the puncture body holder 52 is fastened by moving the fastening member 58 to the rear side in the puncture direction relative to the puncture body holder 52.

Figure 11A:
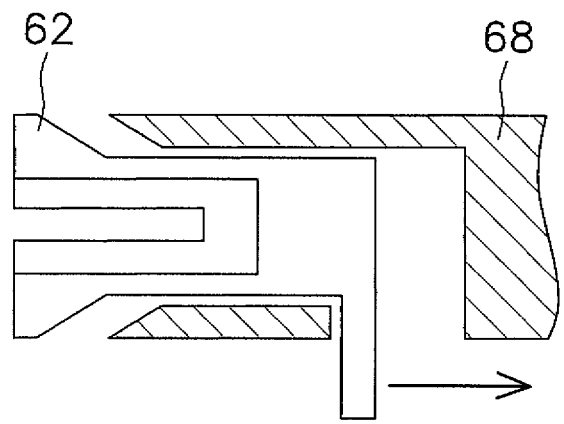
FIGS. 11(a) and 11(b) are sectional side views illustrating conditions of a puncture body holder of a puncture body included in a lancet in accordance with other embodiment of the present invention before and after fastened, respectively.
Figure 11B:
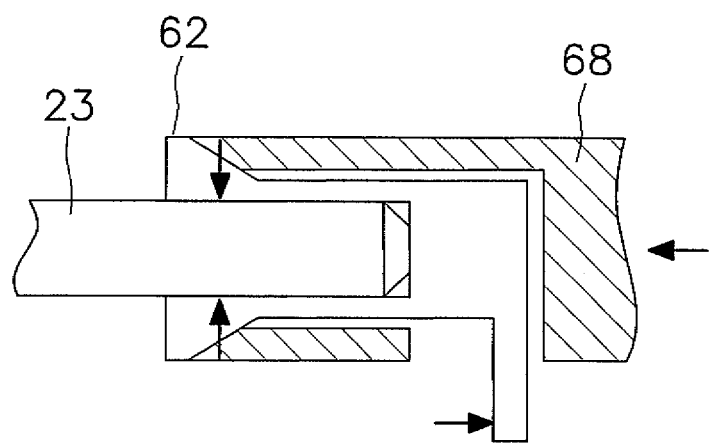

Also, as illustrated in FIGS. 11(a) and 11(b), a configuration may be provided that the puncture body holder 62 is fastened by moving the puncture body holder 62 to the rear side in the puncture direction relative to a fastening member 68.

Figure 13:
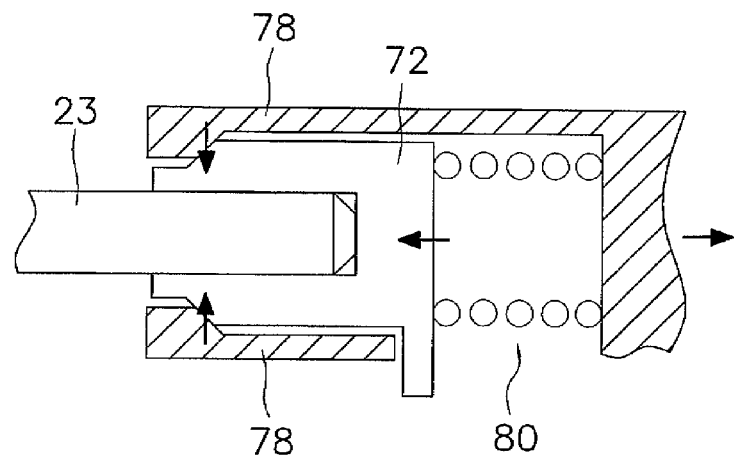
FIG. 13 is a sectional side view illustrating a condition that a lancet body holder of a lancet body of a lancet in accordance with other embodiment of the present invention is fastened by means of a spring.

Also, as illustrated in FIG. 13, it is possible to retain the puncture body while the stable fastening force is kept by urging the puncture body holder 52 or the fastening member 58 to the fastened side of the puncture body holder 52 in the puncture direction with the spring force applied by a coil spring 80 that is provided between a puncture body holder 72 and a fastening member 78.

(E)

As illustrated in FIGS. 8(a) and 8(b), in the above described embodiment, an example is explained that the fastened state of the puncture body holder 32 is released by moving the puncture body holder 32 to the front side in the puncture direction relative to the fastening member 38. However, the present invention is not limited to this configuration.

For example, as illustrated in FIGS. 10(a) and 10(b), a configuration may be provided that the fastened state of the puncture body holder 52 is released by moving the fastening member 58 to the front side in the puncture direction relative to the puncture body holder 52.

Furthermore, as illustrated in FIGS. 11(a) and 11(b), a configuration may be provided that the fastened state of the puncture body holder 62 is released by moving the puncture body holder 62 to the rear side in the puncture direction relative to the fastening member 68.

(F)

In the above described embodiment, an example is explained that the fastening member 38 fastens the puncture body holder 32 by inserting the puncture body 23 into the puncture body holder 32 and then further pressing the puncture body 23 rearward when the lancet 20 is mounted to the main body 30 side. However, the present invention is not limited to this configuration.

Figure 12A:
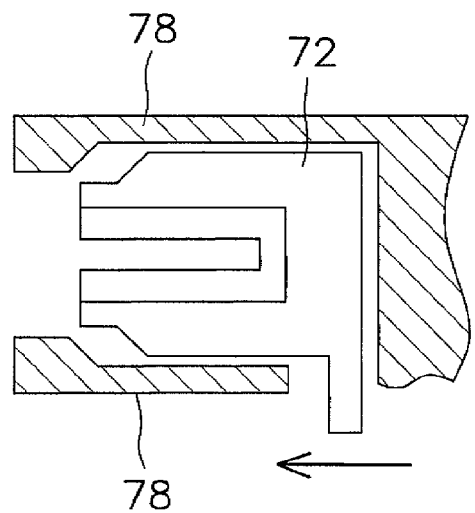
FIGS. 12(a) and 12(b) are sectional side views illustrating conditions of a puncture body holder of a puncture body included in a lancet in accordance with other embodiment of the present invention before and after fastened, respectively.
Figure 12B:
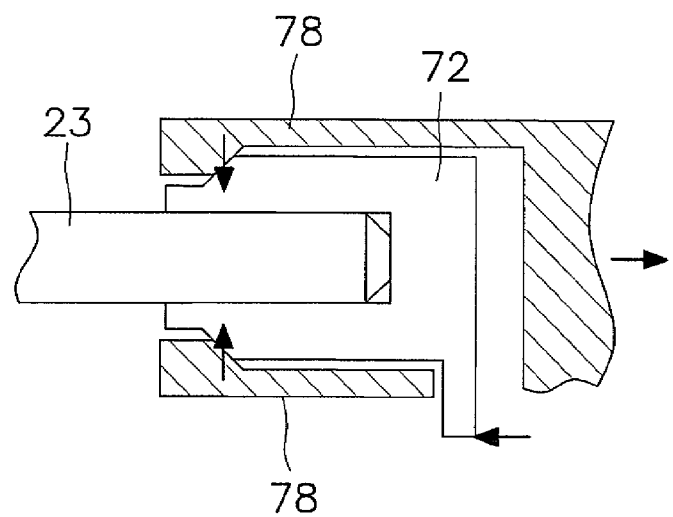

For example, as illustrated in FIGS. 12(a) and 12(b), the puncture body holder 72 may be fastened not with the force for pressing the puncture body 23 rearward but with a portion of the puncture body holder 72, specifically, by moving the puncture body holder 72 forward in the puncture direction with respect to the fastening member 78.

(G)

In the above described embodiment, an example is explained that the abutment 38a is formed in the end portion of the fastening member 38 on the front end side so that the shape of the abutment 38a matches that of the taper portion 32b formed in the puncture body holder 32 on the tip side. However, the present invention is not limited to this configuration.

For example, only the taper portion on the puncture body holder side may be formed, and a portion of the fastening member that makes contact with the taper portion may be a surface parallel to the puncture direction. With this configuration, it is also possible to increase the fastening force in accordance with the movement of the fastening member in the puncture direction. This is because the taper portion is formed to have the outer diameter varying in the puncture direction.

(H)

In the above described embodiment, an example is explained that the POM resin is used as a material for molding the fastening member 38. However, the present invention is not limited to this configuration.

For example, the fastening member may be molded with resin such as nylon or metal such as gunmetal, except for the POM resin.

In addition, in the above described embodiment, an example is explained that the puncture body holder 32 and the puncture body 23 are also molded with PE (polyethylene). However, the present invention is not limited to this configuration.

For example, they may be molded with POM resin that is also used for forming the fastening member or other resin such as PC (polycarbonate) and ABS, except for PE.

(I)

In the above described embodiment, the lancet device 10 including the lancet 20 is explained as an example of the lancet device of the present invention. However, the present invention is not limited to this configuration.

For example, it is possible to apply the lancet device of the present invention to a lancet device that is comprised of the main body side only and does not include the lancet. With this configuration, it is also possible to ensure the sufficient retaining force by fastening the puncture body holder because the fastening member is provided for the main body side.

(J)

In the above described embodiment, an example is explained that the surface of the insertion portion 23*d* of the lancet 20 retained in the puncture body holder 32 is formed in a flat and smooth shape. However, the present invention is not limited to this configuration.

Figure 14:
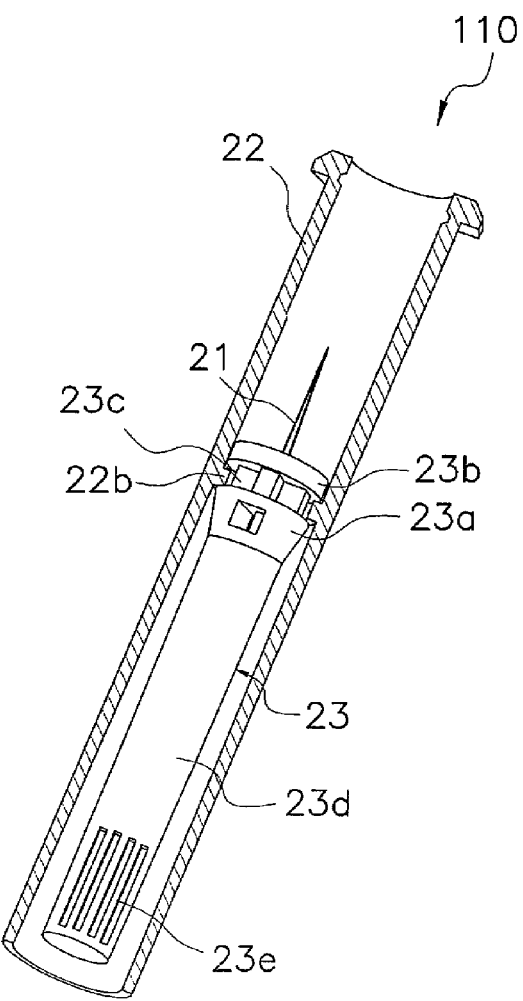
FIG. 14 is a sectional side view illustrating a configuration of a lancet in accordance with other embodiment of the present invention.

For example, as illustrated in FIG. 14, a vertical groove 23*e* may be formed on the surface of the insertion portion 23*d* of a lancet 110. With this configuration, the above described vertical groove 23*e* functions as resistance for blocking rotation of the lancet 110 in the puncture body holder. Accordingly, it is possible to tightly retain the lancet 110 in the puncture body holder, even when the cap 24 is torsionally-sheared, for instance.

Figure 15:
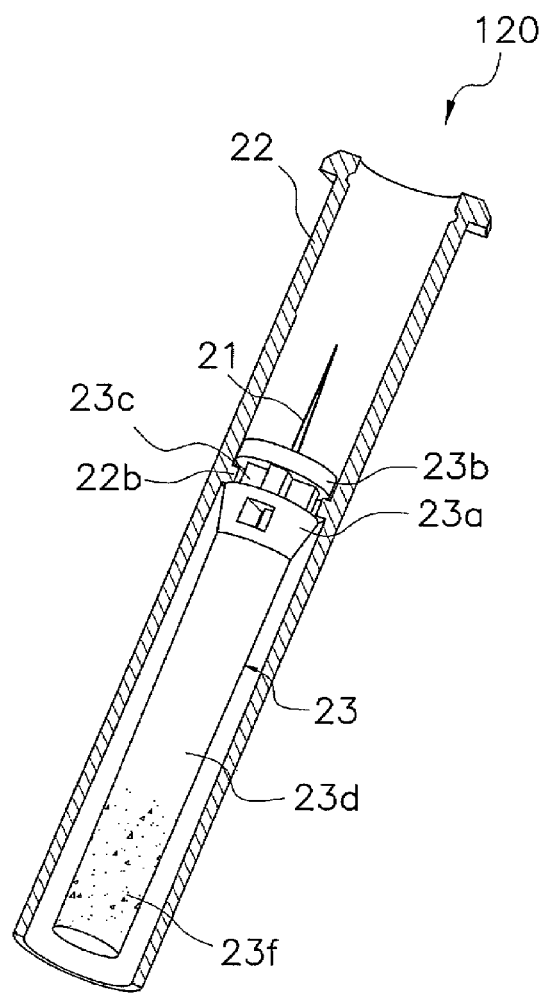
FIG. 15 is a sectional side view illustrating a configuration of a lancet in accordance with other embodiment of the present invention.

Furthermore, as illustrated in FIG. 15, a fine-grained concave-convex 23*f* may be formed on the surface of the insertion portion 23*d* of a lancet 120. With this configuration, the above described concave-convex 23*f* functions as resistance for blocking movement of the lancet 110 in the puncture body holder both in the rotational direction and in the puncture direction. Accordingly, it is possible to tightly retain the lancet 120 in the puncture body holder.

(K)

In the above described embodiment, an example is explained that the surface of the insertion portion 23*d* of the lancet 20 to be retained in the puncture body holder 32 is formed in a flat and smooth shape and the inner peripheral surface of the puncture body holder 32 is also formed in a flat and smooth shape. However, the present invention is not limited to this configuration.

Figure 16:
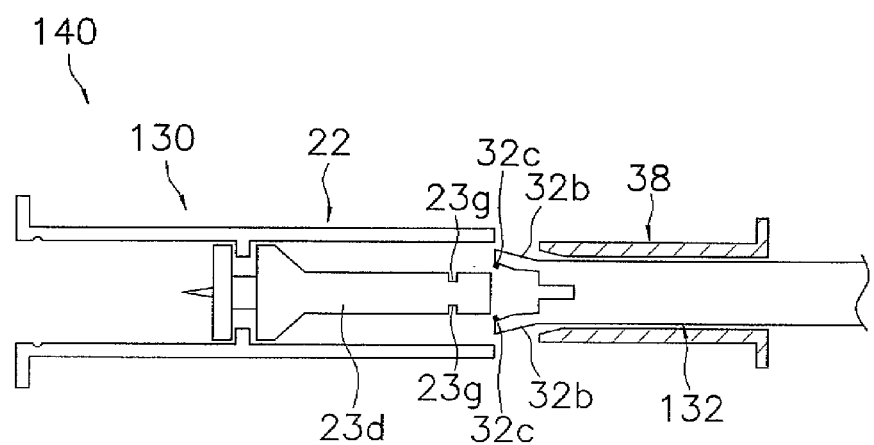
FIG. 16 is a sectional side view illustrating a configuration of a lancet device in accordance with other embodiment of the present invention.

For example, as illustrated in FIG. 16, a lancet device 140 may be provided with a configuration that a concave portion 23*g* is formed on the surface of the insertion portion 23*d* of a lancet 130 and a convex portion 32*c* is formed on the tip of the taper portion 32*b* of the puncture body holder 132, and the concave portion 23*g* and the convex portion 32*c* are engaged with each other. With this configuration, it is possible to tightly retain the lancet 130 in the puncture body holder 132 by means of the above described engaging force generated between the concave portion 23*g* and the convex portion 32*c* and the fastening force for fastening the lancet holder 132 by the fastening member 38.

Figure 17:
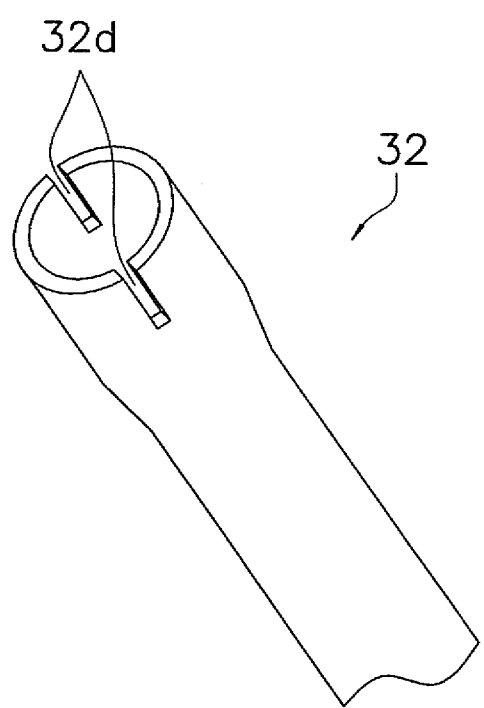
FIG. 17 is a perspective view illustrating a configuration of a lancet body holder included in a lancet device in accordance with other embodiment of the present invention.

Furthermore, as illustrated in FIG. 17, a configuration may be provided that a slit 32*d* is formed in a portion of the puncture body holder 32 in which the insertion portion 20*d* of the lancet 20 is retained and the insertion portion 20*d* of the lancet 20 is fastened and retained when a portion around the slit 32*d* is elastically deformed.

INDUSTRIAL APPLICABILITY

According to the lancet device of the present invention, the following effects are achieved. That is, compared to the conventional lancet device configured to retain the lancet only by means of the frictional force, it is possible to ensure the sufficient retaining force in performing a puncture or the like, and it is also possible to configure a safer lancet device with a simple configuration. Therefore, it is generally applicable to a lancet device used in a variety of fields.

What is claimed is:

1. A lancet device comprising:
   a lancet including a puncture needle mounted to a tip thereof, the lancet being configured to perform a puncture by moving the puncture needle forward in a puncture direction along a longitudinal axis of the lancet device;
   a lancet holder including a mounting portion that deforms inwardly toward the lancet for removably retaining a base end portion of the lancet inserted thereinto; and
   a fastening member configured to make contact with an outer peripheral surface of the mounting potion of the lancet holder for causing the mounting portion of the lancet holder to deform inwardly for retaining the lancet with a frictional force acting in a direction transverse to the longitudinal axis, the frictional force increasing for causing the lancet holder to tightly retain the lancet when the fastening member is moved relative to the lancet holder in a first direction along the longitudinal axis, the frictional force being reduced or removed for causing the lancet holder to release the lancet when the fastening member is moved relative to the lancet holder in a second direction opposite to the first direction along the longitudinal axis.

2. The lancet device according to claim 1, wherein an outer diameter of the base end portion of the lancet and an inner diameter of the mounting portion of the lancet holder are approximately equal.

3. The lancet device according to claim 1, wherein the outer peripheral surface of the mounting portion of the lancet holder and the fastening member are configured to make contact with each other by moving the lancet holder in a retreating direction opposite to the puncture direction relative to the fastening member for retaining the lancet.

4. The lancet device according to claim 3, wherein the lancet is released from the lancet holder by moving the lancet holder in the puncture direction with respect to the fastening member.

5. The lancet device according to claim 3, wherein the mounting portion of the lancet holder includes a flaring front portion that has an outer diameter becoming larger toward the needle in the puncture direction.

6. The lancet device according to claim 1, wherein the outer peripheral surface of the mounting portion of the lancet holder and the fastening member are configured to make contact with each other by moving the fastening member in a retreating direction opposite to the puncture direction relative to the lancet holder for retaining the lancet.

7. The lancet device according to claim 6, wherein the lancet holder is released by moving the fastening member in the puncture direction relative to the lancet holder.

8. The lancet device according to claim 6, wherein the fastening member includes a tapering front portion that has an inner diameter becoming smaller toward the needle in the puncture direction.

9. The lancet device according to claim 1, wherein the fastening member is configured to elastically deform the mounting portion of the lancet holder in the direction transverse to the puncture direction for retaining the lancet.

10. The lancet device according to claim 1, wherein a portion of the base end portion of the lancet to be inserted into the mounting portion of the lancet holder is formed to have a uniform outer diameter in the puncture direction.

11. The lancet device according to claim 1, wherein the lancet comprises:
   a puncture body carrying the puncture needle;
   a casing including a tubular portion and an opening, the tubular portion being configured to accommodate the puncture body while allowing the puncture body to move back and forth along the longitudinal axis, the opening being formed in an end portion of the casing for allowing the puncture needle to protrude beyond the opening in the puncture direction; and
   an engaging portion configured to retain the puncture body in the interior of the casing so that the puncture body is not allowed to move back and forth in the puncture direction after the lancet is removed from the lancet holder.

12. The lancet device according to claim 1, further comprising an urging member, the urging member being provided between the fastening member and the lancet holder, the urging member being configured to urge the lancet holder in the puncture direction.

13. The lancet device according to claim 1, wherein the lancet holder retains the base end portion of the lancet by means of a frictional force.

14. The lancet device according to claim 1, wherein a groove is formed on a surface of the base end portion, the groove being formed along the longitudinal axis.

15. The lancet device according to claim 1, wherein a plurality of concave-convex portions are formed on a surface of the base end portion.

16. The lancet device according to claim 1,
   wherein the base end portion includes a groove formed in a surface of the base end portion for engagement with the fastening member, and
   wherein the fastening member includes a projection configured to engage with the groove.

17. A lancet device comprising:
   a lancet including a puncture needle mounted to a tip thereof, the lancet being configured to perform a puncture by moving the puncture needle forward in a puncture direction along a longitudinal axis of the lancet device;
   a lancet holder including a mounting portion that retains a base end portion of the lancet inserted thereinto; and
   a fastening member configured to make contact with an outer peripheral surface of the mounting potion of the lancet holder for causing the lancet holder to retain the lancet with a frictional force acting in a direction transverse to the longitudinal axis, the frictional force increasing when the fastening member is moved relative to the lancet holder in a first direction along the longitudinal axis, the frictional force being reduced or removed when the fastening member is moved relative to the lancet holder in a second direction opposite to the first direction along the longitudinal axis;
   wherein the outer peripheral surface of the mounting portion of the lancet holder and the fastening member are configured to make contact with each other by moving the lancet holder in a retreating direction opposite to the puncture direction relative to the fastening member for retaining the lancet; and
   wherein the lancet is released from the lancet holder by moving the lancet holder in the puncture direction with respect to the fastening member.

18. A lancet device comprising:
   a lancet including a puncture needle mounted to a tip thereof, the lancet being configured to perform a puncture by moving the puncture needle forward in a puncture direction along a longitudinal axis of the lancet device;
   a lancet holder including a mounting portion that deforms inwardly toward the lancet for removably retaining a base end portion of the lancet inserted thereinto; and
   a fastening member configured to make contact with an outer peripheral surface of the mounting potion of the lancet holder for causing the mounting portion of the lancet holder to deform inwardly for retaining the lancet with a frictional force acting in a direction transverse to the longitudinal axis, the frictional force increasing when the fastening member is moved relative to the lancet holder in a first direction along the longitudinal axis, the frictional force being reduced or removed when the fastening member is moved relative to the lancet holder in a second direction opposite to the first direction along the longitudinal axis;
   wherein the outer peripheral surface of the mounting portion of the lancet holder and the fastening member are configured to make contact with each other by moving the fastening member in a retreating direction opposite to the puncture direction relative to the lancet holder for retaining the lancet; and
   wherein the fastening member includes a tapering front portion that has an inner diameter becoming smaller toward the needle in the puncture direction.

19. A lancet device comprising:
   a lancet including a puncture needle mounted to a tip thereof, the lancet being configured to perform a puncture by moving the puncture needle forward in a puncture direction along a longitudinal axis of the lancet device;
   a lancet holder including a mounting portion that deforms inwardly toward the lancet for removably retaining a base end portion of the lancet inserted thereinto; and
   a fastening member configured to make contact with an outer peripheral surface of the mounting potion of the lancet holder for causing the mounting portion of the lancet holder to deform inwardly for retaining the lancet with a frictional force acting in a direction transverse to the longitudinal axis, the frictional force increasing when the fastening member is moved relative to the lancet holder in a first direction along the longitudinal axis, the frictional force being reduced or removed when the fastening member is moved relative to the lancet holder in a second direction opposite to the first direction along the longitudinal axis; and
   an urging member provided between the fastening member and the lancet holder, the urging member being configured to urge the lancet holder in the puncture direction.

20. A lancet device comprising:
   a lancet including a puncture needle mounted to a tip thereof, the lancet being configured to perform a puncture by moving the puncture needle forward in a puncture direction along a longitudinal axis of the lancet device;
   a lancet holder including a mounting portion that deforms inwardly toward the lancet for removably retaining a base end portion of the lancet inserted thereinto; and
   a fastening member configured to make contact with an outer peripheral surface of the mounting potion of the lancet holder for causing the mounting portion of the lancet holder to deform inwardly for retaining the lancet with a frictional force acting in a direction transverse to the longitudinal axis, the frictional force increasing when the fastening member is moved relative to the lancet holder in a first direction along the longitudinal axis, the frictional force being reduced or removed when the fastening member is moved relative to the lancet holder in a second direction opposite to the first direction along the longitudinal axis;

wherein the lancet holder retains the base end portion of the lancet by means of the frictional force.

21. A lancet device comprising:

a lancet including a puncture needle mounted to a tip thereof, the lancet being configured to perform a puncture by moving the puncture needle forward in a puncture direction along a longitudinal axis of the lancet device;

a lancet holder including a mounting portion that deforms inwardly toward the lancet for removably retaining a base end portion of the lancet inserted thereinto; and a fastening member configured to make contact with an outer peripheral surface of the mounting potion of the lancet holder for causing the mounting portion of the lancet holder to deform inwardly for retaining the lancet with a frictional force acting in a direction transverse to the longitudinal axis, the frictional force increasing when the fastening member is moved relative to the lancet holder in a first direction along the longitudinal axis, the frictional force being reduced or removed when the fastening member is moved relative to the lancet holder in a second direction opposite to the first direction along the longitudinal axis;

wherein the base end portion includes a groove formed in a surface of the base end portion for engagement with the fastening member, and wherein the fastening member includes a projection configured to engage with the groove.

* * * * *